(12) United States Patent
Watanabe

(10) Patent No.: US 6,512,812 B2
(45) Date of Patent: Jan. 28, 2003

(54) X-RAY FOREIGN-BODY DETECTOR

(75) Inventor: Toshihisa Watanabe, Atsugi (JP)

(73) Assignee: Anritsu Corporation, Tokyo (JP)

( * ) Notice: Subject to any disclaimer, the term of this patent is extended or adjusted under 35 U.S.C. 154(b) by 78 days.

(21) Appl. No.: 09/841,384

(22) Filed: Apr. 24, 2001

(65) Prior Publication Data

US 2001/0036247 A1 Nov. 1, 2001

(30) Foreign Application Priority Data

Apr. 28, 2000 (JP) .......................... 2000-130927
Apr. 28, 2000 (JP) .......................... 2000-130928

(51) Int. Cl.[7] ............................... G01N 23/04
(52) U.S. Cl. ........................... 378/57; 378/208
(58) Field of Search ..................... 378/57, 58, 208, 378/210

(56) References Cited

U.S. PATENT DOCUMENTS 5,428,657 A * 6/1995 Papanicolopoulos et al. . 378/86
6,023,497 A * 2/2000 Takahashi et al. ............ 378/53
6,347,131 B1 * 2/2002 Gusterson .................... 378/51
6,370,223 B1 * 4/2002 Gleason et al. .............. 378/54

FOREIGN PATENT DOCUMENTS

| JP | 11-183407 | 7/1999 |
| JP | 11-194104 | 7/1999 |

* cited by examiner

*Primary Examiner*—David P. Porta
*Assistant Examiner*—Courtney Thomas
(74) *Attorney, Agent, or Firm*—Frishauf, Holtz, Goodman & Chick, P.C.

(57) ABSTRACT

An X-ray detection unit integrally includes an X-ray detection part, which detects X-rays and a conveyor part, which conveys an object to be inspected, for detecting a foreign body contained in the object by receiving the X-rays, which are radiated from an X-ray generation part to the object conveyed by the conveyor part and are transmitted through the object, by means of the X-ray detection part, the X-ray detection part and the conveyor part being integrally attached to a predetermined part in a casing, such that the X-ray detection part and the conveyor part are freely attachable and detachable. The X-ray detection unit comprises an X-ray detection part container made of metal, front and rear roller support parts, front and rear rollers and a conveyor belt.

15 Claims, 16 Drawing Sheets

X-RAY FOREIGN-BODY DETECTOR

CROSS-REFERENCE TO RELATED APPLICATIONS

This application is based upon and claims the benefit of priority from the prior Japanese Patent Applications No. 2000-130927, filed Apr. 28, 2000; and No. 2000-130928, filed Apr. 28, 2000, the entire contents of both of which are incorporated herein by reference.

BACKGROUND OF THE INVENTION

The present invention relates to an X-ray object detector in which an object to be detected is fed between an X-ray generation part and an X-ray detection part, for receiving X-rays from the X-ray generation part by a conveyer part, and the X-rays which penetrate the object are received by the X-ray detection part, thereby to detect a foreign body or body (contaminant) contained in the object. Particularly, the present invention relates to an X-ray foreign-body detector which uses an X-ray detection unit comprising integrally the X-ray detection part and the conveyor part.

Conventionally, an X-ray foreign-body detector is used to detect foreign bodies (metal, bones, glass, stones, synthetic resin bodies, and the like) which may be erroneously mixed in an object such as fresh meat, processed food, or the like to be subjected to detection.

In this kind of X-ray foreign-body detector, the X-ray generation part is generally installed on the body of the apparatus, and the X-ray generation part is positioned in the lower side of the X-ray generation part in the body of the apparatus.

In this manner, X-rays radiated from the X-ray generation part are received by the X-ray detection part.

Also, the apparatus body is equipped with a conveyor part for feeding an object to be detected under the X-rays radiated as described above.

This conveyor part includes a plurality of rollers provided at front-side and rear-side positions in the conveying direction in the body of the apparatus, and a belt tensioned around the plurality of rollers.

Any of the plurality of rollers serves as a drive roller which is connected with and driven by a drive source such as a motor or the like attached to the apparatus body, and the other rollers serve as slave rollers which are driven by the drive roller.

By driving of the plurality of rollers, the belt tensioned around the plurality of rollers is circularly rotated.

A support plate for supporting the object to be detected is provided in a belt rotated circularly.

Also, the X-ray detection part is provided in the lower side of the belt (e.g., inside the belt rotated circularly).

Further, the upper side of the belt is situated between the x-ray generation part and the X-ray detection part.

In this manner, in the X-ray foreign-body detector, the X-ray generation part radiates X-rays to the object to be detected, which is conveyed on the belt, and the X-ray detection part receives the X-rays, which have penetrated the object to be detected, thereby to detect a foreign body contained in the object to be detected.

However, in the conventional x-ray foreign-body detector described above, the X-ray generation part, x-ray detection part, and conveyor part are attached to the apparatus body.

In particular, the X-ray detection part and the conveyor part are situated to be close to each other, in order to detect a foreign body mixed in the conveyed object subjected to detection.

Therefore, the structure is arranged such that the rollers, belt, support plate, drive source (motor), and the like as components forming the conveyor part are provided and mixed together with the X-ray detection part, at the part of the apparatus body where the X-ray detection part and the conveyor part are installed.

If components having functions different from each other are thus mixed, assembly of the components is complicated and much labor is required for maintenance such as inspecting, repairing, cleaning, and the like, of respective parts.

In particular, with respect to cleaning, food is inspected as an object subjected to detection in some cases. Care is therefore required to maintain hygiene.

However, since the structure is arranged such that components forming the X-ray detection part and the conveyor part are in close proximity as described above, there is a problem in that gaps and seams between component allow for germs to multiply therein.

Although the components need to be disassembled to clean the gaps and seams, the structure is arranged such that the components forming the X-ray detection part and conveyor part combined.

Therefore, in the conventional x-ray foreign-body detector, there is a problem that the respective components cannot be easily disassembled during cleaning.

In addition, in the conventional X-ray foreign-body detector, the X-ray generation part, x-ray detection part, and conveyor part are installed on the apparatus body.

Therefore, the x-ray generation part, X-ray detection part, and conveyor part cannot be assembled without the apparatus body.

That is, in the conventional X-ray foreign-body detector, assembly processes constitute one line which cannot be dispersed into a plurality of lines, resulting in a problem that the manufacturing costs are increased.

FIGS. 16A and 16B are top and side views showing a conventional conveyor.

This conveyor 51 is constructed by a body 52 and an attachable/detachable unit 53 which can be freely attached to and detached from the body 52.

The body 52 is constructed by a pair of side plates 52a and a drive motor 57.

The attachable/detachable unit 53 is constructed by a receive base 54, a drive roller 55a and a slave roller 55b provided in both side parts of the receiver base 54, and a belt 56 tensioned around the rollers 55a and 55b.

This attachable/detachable unit 53 is kept attached to the body 52, by a fixing tool (for example, a catch clip) 59.

Note that the drive motor 57 is connected with a rotation shaft of the drive roller 55a through a connection belt 58 in order to transmit the rotation of the drive motor 57 to the drive roller 55a.

With respect to the conveyor 51, maintenance and checks must be carried out. For example, the components of the attachable/detachable unit 53 (e.g., the drive roller 55a and the belt 56) must be periodically cleaned or replaced.

Particularly in the case where the object subjected to inspection is food, parts of the conveyor 51 must be sterilized, disinfected, or the like.

However, in the structure described above, the drive roller 55a or the belt 56 cannot be easily attached or detached, so that disassembly, cleaning, and maintenance cannot be carried out easily.

That is, to detach the belt 56, the connection belt 58 tensioned around the drive roller 55*a* and the drive motor 57 must be detached.

For example, when screws of the base of the drive motor 57 and the connection belt 58 are detached, a protection cover 58*a* of the (safety) connection belt 58*a* must be detached in order to detach the connection belt 58.

At this time, in the state where the protection cover 58*a* is detached, a risk arises in that the connection belt 58 is openly exposed.

In order to solve this problem, another structure is arranged such that transmission of the drive force between the drive roller 55*a* and the drive motor 57 of the conveyor 51 is not achieved by the connection belt 58, but is achieved by providing gears respectively for the drive roller 55*a* and the drive motor 57, to make connection by engagement of the gears.

Thus, also in this structure of using gears, the gears are engaged with each other at a predetermined pitch (precision), and therefore, it is difficult that the conveyor 51 is connected and disconnected by the gear parts.

In this case, if the tooth engagement precision is relaxed by changing the shape of the gears etc., the conveyor 51 can be easily detachable at the gear part. There is however a problem that the transmission characteristics (efficiency and durability) of the drive force are lowered.

BRIEF SUMMARY OF THE INVENTION

The present invention has an object of providing an X-ray foreign-body detector which uses an X-ray detection unit integrally comprising an X-ray detection part and a conveyor part, in order to achieve discreet assembly of each component, and to facilitate maintenance.

Another object of the present invention is to provide an X-ray foreign-body detector which uses an X-ray detection unit integrally comprising an X-ray detection part and a conveyor part in order to achieve discreet assembly of each component and to facilitate maintenance, and which also uses a conveyor which can be disassembled for cleaning or the like through a simple structure.

Further, another object of the present invention is to provide an X-ray foreign-body detector which uses an X-ray detection unit integrally comprising an X-ray detection part and a conveyor part in order to achieve discreet assembly of each component and to facilitate maintenance, and which also uses such a conveyor part in which the conveying distance can be freely changed according to needs.

To achieve the above objects, according to the first aspect of the present invention, there is provided an X-ray foreign-body detector comprising:

a casing (5);

an X-ray generation part (1) provided inside the casing; and an X-ray detection unit (100) integrally including an X-ray detection part (2), which detects X-rays, and, a conveyor part (3), which conveys an object to be inspected, for detecting a foreign body mixed in the object by receiving the X-rays, which are radiated from the X-ray generation part to the object conveyed by the conveyor part and are transmitted through the object, the X-ray detection part and the conveyor part being integrally attached to a predetermined part of the casing, such that the X-ray detection part and the conveyor part are freely attachable and detachable, wherein the X-ray detection unit comprises an X-ray detection part container (6) made of metal, which has at least an upper surface (6*a*), a lower surface (6*e*) opposed to the upper surface, and front and rear surfaces (6*b* and 6*c*) which connect the upper and lower surfaces in both sides in a longitudinal direction, and in which a slit (7) extending in a lateral direction to allow the X-rays to penetrate through the upper surface (6*a*) is formed in the upper surface, and the X-ray detection part is provided inside, a front roller support part (11) extending forward in the longitudinal direction of the X-ray detection part container and attached to the X-ray detection part container, a rear roller support part (12) extending rearward in the longitudinal direction of the X-ray detection part container and attached to the x-ray detection part container, a front roller (8) detachably and attachably included in the front roller support part, a rear roller (8) detachably and attachably included in the rear roller support part, and a conveyor belt (10) tensioned around the front and rear rollers, surrounding the X-ray detection part container, and supported on the upper surface of the X-ray detection part container in a state in which the object is mounted thereon, one of the front and rear rollers being constructed as a drive roller and the other one being constructed as a slave roller.

To further achieve the above objects, according to the second aspect of the present invention, in the detector according to the first aspect, the X-ray detection unit further comprises a drive roller unit provided in parallel with the drive roller, a drive roller, a pair of bearing parts provided at both ends of the drive roller, and a fixing shaft to which the pair of bearing parts are fixed, the drive roller unit being detachably attached to the X-ray detection part container.

To further achieve the above objects, according to the third aspect of the present invention, in the detector according to the second aspect, the X-ray detection part container is provided with engaging grooves in which with one of the bearing parts and the fixing shafts are engaged and positioned to fix the drive roller unit.

To further achieve the above objects, according to the fourth aspect of the present invention, in the detector according to the second aspect of the present invention, the X-ray detection part container is provided with a fixing mechanism which is engaged with the fixing shaft thereby to fix and hold the drive roller unit in relation to the casing.

To further achieve the above objects, according to the fifth aspect of the present invention, in the detector according to the second aspect, the X-ray detection unit further comprises a connection part provided at an end part of a rotation shaft of the drive roller, to transmit the drive force of the motor and to enable separation, such that the drive roller unit can be freely detached and attached by the separation at the connection part.

To further achieve the above objects, according to the sixth aspect of the present invention, in the detector according to the fifth aspect, the connection part is constructed by a pair of couplings fixed respectively to an output shaft of the motor and the rotation shaft of the drive roller, thus transmitting the drive force.

To further achieve the above objects, according to seventh aspect of the present invention, in the detector according to the sixth aspect of the present invention, the x-ray detection unit further comprises a protection case and a receiving section provided for the drive roller and the motor, such that the protection case and the receiving section are respectively coaxial with the pair of couplings, enable positioning of axles of the pair of couplings, and cover the pair of couplings.

To further achieve the above objects, according to the eighth aspect of the present invention, in the detector according to the second aspect, the X-ray detection part is sealed and contained in the X-ray detection part container.

To further achieve the above objects, according to the ninth aspect of the present invention, in the detector according to the eighth aspect, one slave roller among the one driver roller and three slave rollers is arranged at a side part of the X-ray detection part container, the other two slave rollers of the three slave rollers are arranged at another side part of the X-ray detection part container.

To further achieve the above objects, according to the tenth aspect of the present invention, in the detector according to the ninth aspect, engaging grooves in which the two slave rollers arranged at the another side part are engaged are formed in the X-ray detection part container, and a slide plate which can be freely slid is provided in a side of the one side parts.

In the structure described above, bearing parts at both end parts of the drive roller of the conveyor part are integrated by a fixing shaft, and these parts are detachably attached to the X-ray detection part container.

The engaging grooves provided in the X-ray detection part container position the bearing parts and the fixing shaft, so that they can be easily and freely attached to or detached from the casing by operating a fixing mechanism.

In addition, the motor and the rotation shaft of the drive roller can be connected and disconnected by couplings, so the connection and disconnection of the drive force transmission part can be easily carried out. Accordingly, the drive roller unit can be detached and attached more easily.

To further also achieve the above objects, according to the eleventh aspect of the present invention, in the detector according to the first aspect, the roller support parts corresponding to a conveying distance are respectively installed at positions at the front and rear of the X-ray detection part container, and a conveyor belt having a corresponding conveying distance is installed at the same time, thereby making the conveying distance freely changeable.

To further achieve the above objects, according to the twelfth aspect of the present invention, in the detector according to the tenth aspect, the X-ray detection part container is provided with a cover which has a length corresponding to the conveying distance of the conveyor part and prevents leakage of X-rays.

To further achieve the above objects, according to the thirteenth aspect of the present invention, in the detector according to the tenth aspect, an engaging part for engaging and releasing each of the X-ray detection part container and the front and rear roller support parts is provided on a joint surface between the X-ray detection part container and the front and rear roller support parts.

To further achieve the above objects, according to the fourteenth aspect of the present invention, in the detector according to the tenth aspect, a detachably attached drive roller unit, for conveying and driving the conveyor belt, is provided at the front and rear roller support parts, and the drive roller unit comprises a pair of bearing parts provided at both ends of the drive roller, and a fixing shaft provided in parallel with the drive roller, for making the pair of bearing parts respectively fixed to the fixing shaft.

To further achieve the above objects, according to the fifteenth aspect of the present invention, in the detector according to the thirteenth aspect, a connection part which transmits the drive force of a motor, and can be freely separated, is provided at an end part of a rotation shaft of the drive roller.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
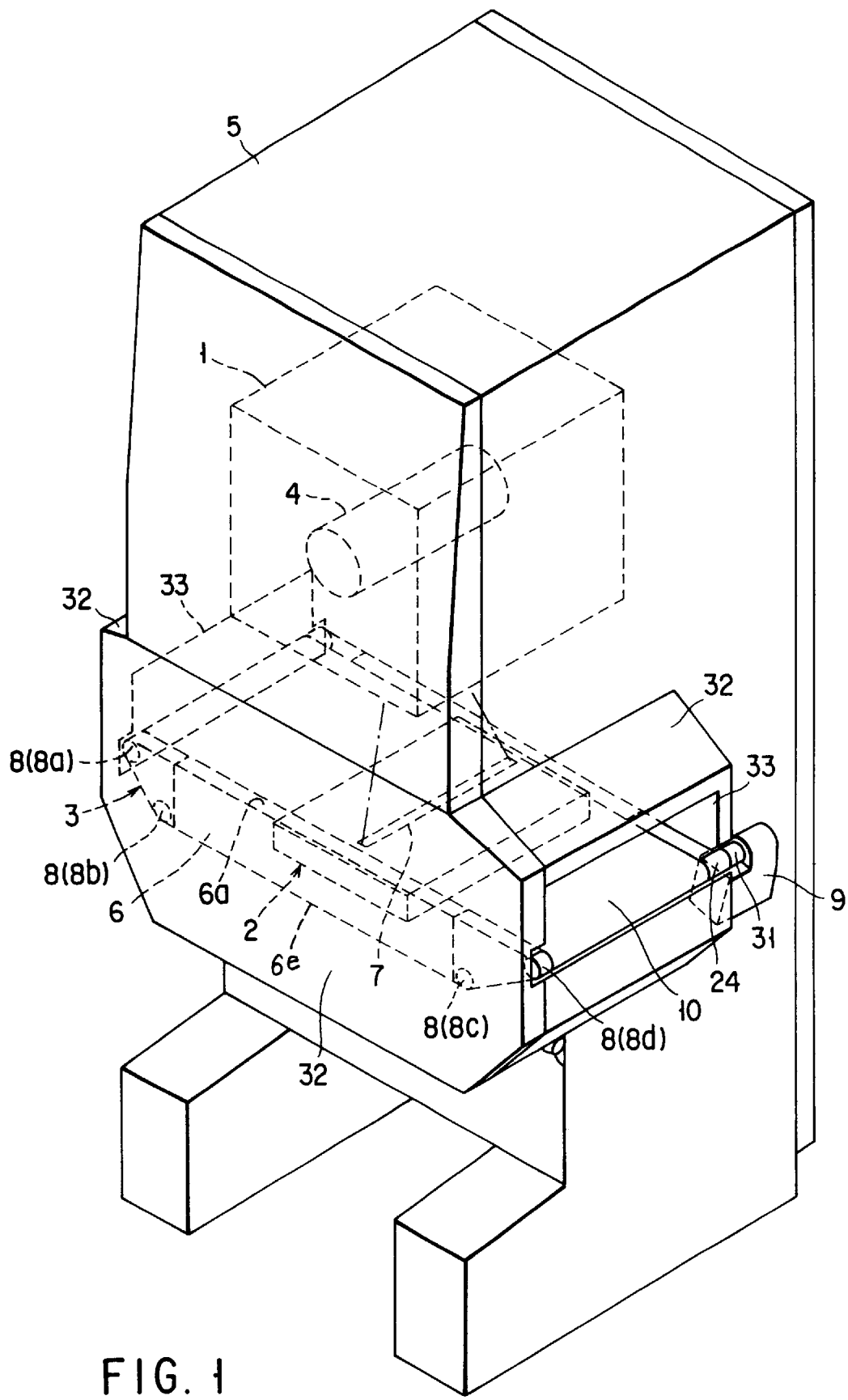
FIG. 1 is a perspective view showing the entire structure of the first embodiment of an X-ray foreign-body detector according to the present invention.

Reference will be made in detail to the presently preferred embodiments of the invention as illustrated in the accompanying drawings, in which like reference numerals designate like or corresponding parts.

Several embodiments of the present invention will now be specifically explained below with reference to the drawings.

(First Embodiment)

FIG. 1 shows the entire structure of the first embodiment of an X-ray foreign-body detector according to the present invention.

Figure 2:
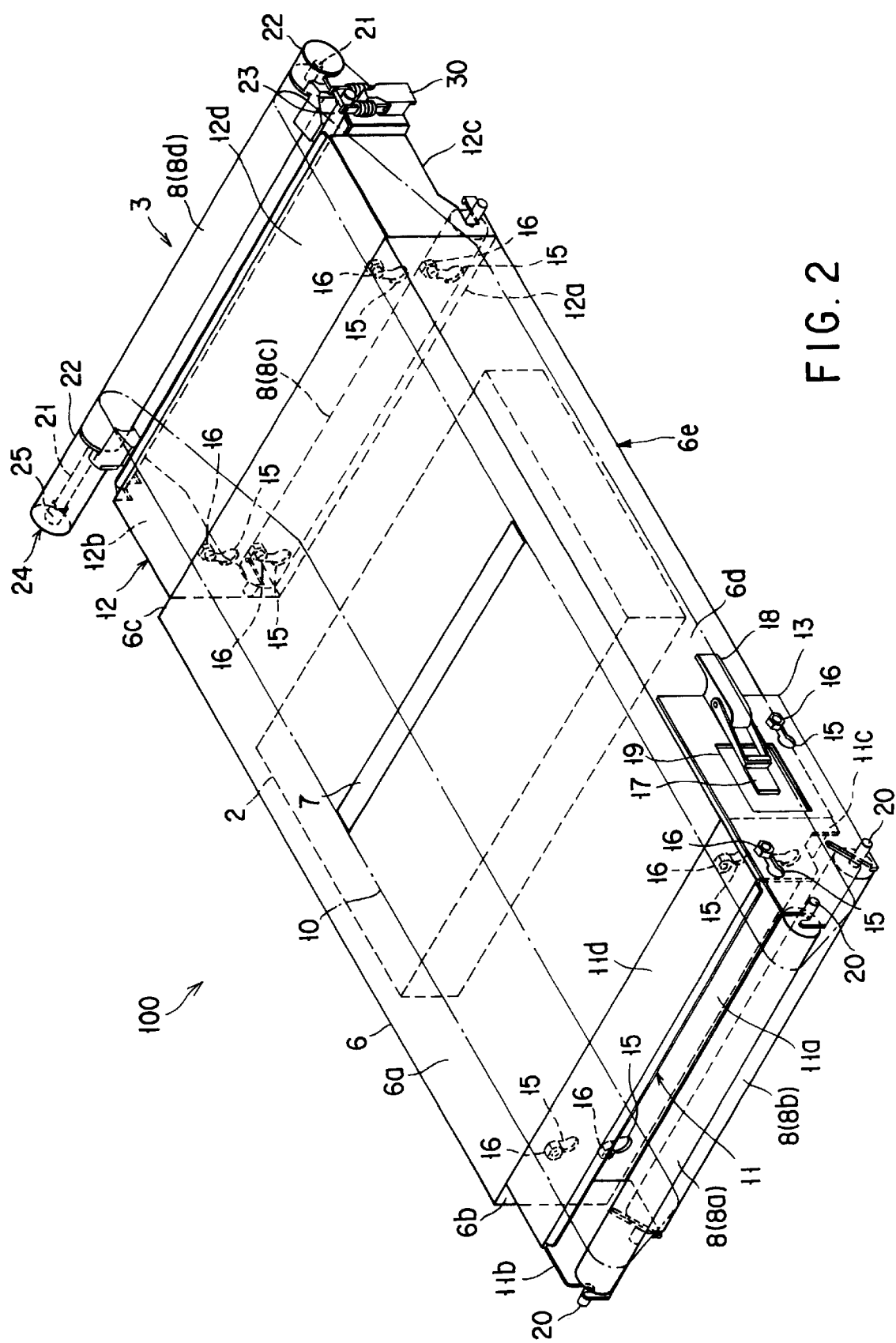
FIG. 2 is a perspective view showing the structure of an X-ray detection unit shown in FIG. 1.

FIG. 2 shows the structure of the X-ray detection unit shown in FIG. 1.

Figure 3:
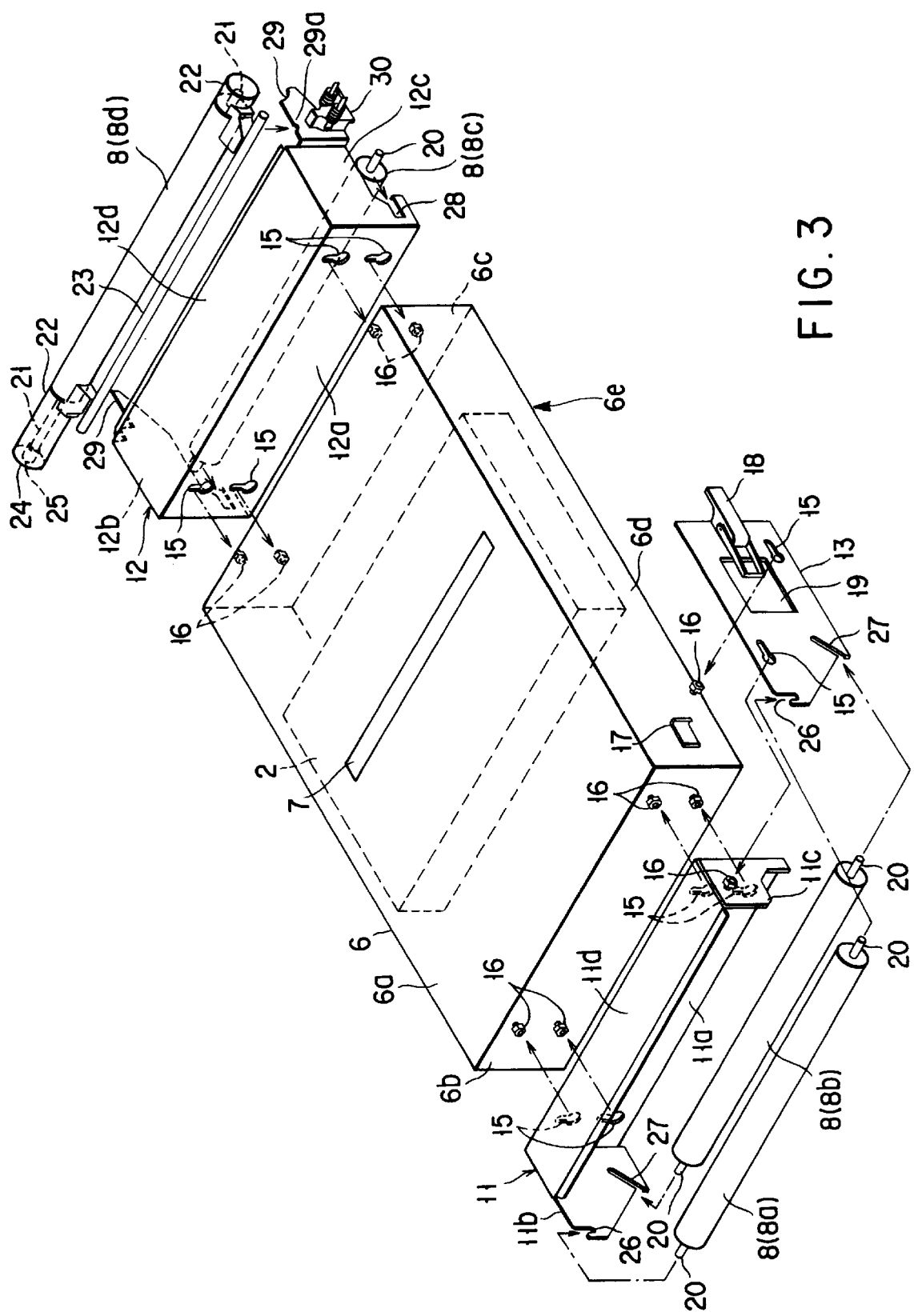
FIG. 3 is an exploded perspective view of the X-ray detection unit shown in FIG. 2.

FIG. 3 shows an exploded perspective view of the X-ray detection unit shown in FIG. 2.

As shown in FIG. 1, the X-ray foreign-body detector is mainly comprised of an X-ray generation part 1 for generating X-rays, and a conveyor part 3 for conveying an object (not shown) subjected to detection, to between the X-ray generation part 1 and the X-ray detection part 2.

The X-ray generation part 1 is constructed so as to prevent leakage of X-rays by covering the periphery of an X-ray tube 4 which generates X-rays, with a shielding plate.

This shielding plate is constructed by internally adhering a shielding body such as lead or the like.

The X-ray generation part 1 is provided at an upper part of a casing 5 forming part of the X-ray foreign-body detector and radiates X-rays downward.

At this time, an X-ray is radiated and spread substantial conically downward from the X-ray tube 4. Thereafter, the X-rays passes thorough a long hole formed in the bottom part of the X-ray generation part 1 and a long hole provided in the bottom plate in the side of the casing 5 which supports the X-ray generation part 1, and is thereafter radiated in a planar shape spreading downward, as indicated by the dashed line in FIG. 1.

Also, in the X-ray generation part 1, heat caused when X-rays are generated is radiated through a cooling fin (not shown).

The X-ray detection part 2 is provided at a lower part of the casing 5 forming part of the X-ray foreign-body detector, and is constructed so as to receive X-rays radiated from the X-ray generation part 1.

This X-ray detection part 2 is contained in an X-ray-detection-part container (hereinafter called a metal box) 6 made of metal and shaped like a box.

This metal box 6 has a slit 7 in the upper surface 6a formed to be substantially flat.

This slit 7 is constructed by attaching a resin body, which transmits the X-rays and is water-proofed by a silicon body or the like, to a long hole which is formed in the plate metal of the upper surface 6a such that the hole extends in a lateral direction.

This slit 7 allows the planar X-ray radiated from the X-ray generation part 1 to pass through.

Specifically, the lateral direction in which the slit 7 is formed is a direction in which the planar X-rays can be transmitted and perpendicular direction to the conveying direction for the object to be inspected.

Note that the metal box 6 need not always be a hexahedron but may be constructed at least as an X-ray-detection-part container made of metal, which has an upper surface 6a, a lower surface 6e opposed to the upper surface, and front and rear surfaces 6b and 6c which connect the upper and lower surfaces in both sides in the longitudinal direction, such that the slit 7 is formed in the upper surface (6a) so as to extend in the lateral direction to left the X-rays pass through, and that the X-ray detection part 2 is provided inside.

Further, the X-ray which has passed through the slit 7 of the metal box 6 is received by the X-ray detection part 2 provided in the metal box 6.

This X-ray detection part 2 performs optical/electrical energy-converting on the X-rays and outputs it to an X-ray processing part not shown.

One side surface of the metal box 6 in the lateral direction is fixed to or detachably fixed to the casing 5 forming part of the body of the X-ray foreign-body detector.

In the present embodiment, the one side and the other side of the metal box 6 in the lateral direction are fixed to the casing 5 by welding. However, the metal box 6 may be fixed in a different manner from welding, e.g., a manner using a bolt, etc.

In addition, the metal box 6 may be equipped with legs 34 and placed on a plane, as will be described later.

As shown in FIG. 1, the conveyor part 3 is mainly constructed by a roller 8, a motor unit 9, and a conveyor belt 10.

As shown in FIGS. 2 and 3, the roller 8 and the conveyor belt 10 forming part of the conveyor part 3 are attached to the metal box 6 which contains the X-ray detection part 2.

As shown in FIG. 2, the slit 7 is provided in the upper surface 6a of the metal box 6 in a lateral direction. The direction which is perpendicular to the slit 7 is the longitudinal direction.

A front roller support part 11 and a rear roller support part 12 are provided in the front surface 6b and the rear surface 6c of the metal box 6 situated in the front and rear sides in the longitudinal direction.

The front roller support part 11 is constructed by a fixing plate 11a, a pair of support members 11b and 11c bent and extended in parallel at both side parts of the fixing plate 11a, and a support plate 11d also bent and extended at an upper part of the fixing plate 11a, as shown in FIG. 3.

Further, the front roller support part 11 further comprises a side plate 13 which has a different structure than the fixing plate 11a, the support members 11b and 11c, and the support plate 11d.

A plurality of (four) holes 15 including a small diameter part and a large diameter part continuous to each other are provided in the fixing plate 11a.

In this respect, engaging parts 16 comprised of collars, which engage with the small-diameter parts of the holes 15 in the fixing plate 11a, bolts, which are inserted in the large-diameter parts of the holes 15 in the fixing plate 11a, and washers are provided on the front surface 6b of the metal box 6.

That is, the fixing plate 11a hangs on the front surface 6b of the metal box 6 by engaging the holes 15 with the bolts and washers of the engaging parts 16 and by engaging them with the collars of the engaging parts 16.

In this manner, the front roller support part 11 detachably attached on the front surface 6b of the metal box 6.

The side plate 13 is set so as to bridge the side surface 6d of the metal box 6 and the support member 11c, as shown in FIG. 3.

A plurality of (two) holes 15 each having a small-diameter part and a large diameter part continuous to each other are provided in the side plate 13.

In this respect, engaging parts 16 comprised of collars, which engage with the small-diameter parts of the holes 15 in the side plate 13, bolts, which are inserted in the large-diameter parts of the holes 15, and washers are provided on the side surface 6d and the supporting member 11c.

That is, the side plate 13 hangs on the side surface 6d of the metal box 6 and the support member 11c by engaging the holes 15 with the bolts and washers of the engaging parts 16 and by engaging them with the collars of the engaging parts.

Also, the side plate 13 is provided with a fixing hook 18 such as a catch clip or the like which engages with the hook 17 provided on the side surface 6d of the metal box 6.

Further, the hook 17 is exposed from an opening hole 19 existing in the side plate 13, when the side plate 13 is set on the side surface 6d and the support member 11c.

The fixing mechanism 18 is engaged with the exposed hook 17.

By engaging this fixing mechanism 18 with the hook 17, the side plate 13 slides such that the small-diameter parts of the holes 15 are engaged with the collars of the engaging parts 16.

In addition, by releasing the fixing mechanism 18 engaged with the hook 17 and by releasing the bolts and washers of the engaging parts 16 from the holes 15, it is possible to achieve easy detachment from the side surface 6d of the metal box 6.

In this manner, the support port of the slave rollers 8a and 8b is constructed by the side plate 13 attached to the side surface 6d of the metal box 6 together with the front roller support part 11 hanged to the side surface 6b of the metal box 6.

In the embodiment, the side plate 13 is provided to extend the front roller support port 11 and the metal box 6 from the front direction. However the side plate 13 may be provided to one of the front support port 11 and the metal box 6 from the front direction.

Further, as shown in FIG. 3, the rear roller support part 12 is constructed by a fixing plate 12a, a pair of support members 12b and 12c bent and extended in parallel at both side parts of the fixing plate 12a, and a support plate 12d also bent and extended at an upper part of the fixing plate 12a.

A plurality of (four) holes 15 each having a small-diameter part and a large diameter part continuous to each other are provided in this fixing plate 12a.

In this respect, engaging parts 16 comprised of collars, which are engaged in the small-diameter parts of the holes 15 of the fixing plate 12a and in the rear surface 6c of the metal box 6, bolts, which are inserted in the large-diameter parts, and washers are provided in the rear surface 6c of the metal box 6.

Specifically, the fixing plate 12a hangs on the rear surface 6c of the metal box 6 by engaging the holes 15 with the bolts and washers of the engaging parts 16 and by engaging them with the collars of the engaging parts 16.

In this manner, the rear roller support part 12 is detachably/attachably set on the rear surface 6c of the metal box 6 extend to the longitudinal direction from the rear surface 6c.

When the front roller support part 11 and the rear roller support part 12 are fixed to the metal box 6, the support plates 11d and 12d are situated in the same plane as the upper surface 6a of the metal box 6.

The rollers 8 are supported by the front roller support part 11 and the rear roller support part 12 fixed to the metal box 6, as described above.

As shown in FIGS. 2 and 3, a total of four rollers 8 are provided. Among them, three rollers 8a, 8b, and 8c serve as slave rollers, and the remaining one roller 8d serves as a drive roller.

In this case, each of the rollers 8a, 8b, and 8c as slave rollers is freely rotatable about its roller shaft 20 projecting from both sides by bearings (not shown) provided inside.

The roller 8d as a drive roller has a rotation shaft 21 projecting from both ends thereof and is supported by bearing parts 22 internally provided with bearings (not shown) such that the roller 8d is freely rotatable.

The bearing parts 22 are fixed to the fixing shaft 23 provided in parallel the rotation shaft 21, by screws.

Also, one of the bearing parts 22 constructs a cylindrical connection part 24 from which an end part of the rotation shaft 21 accommodated therein is exposed.

One of pared male and female couplings 25, which is connected with the output shaft side of the motor unit 9 described later, is fixed to the exposed end part of the rotation shaft 21.

Among the rollers 8 described above, the roller 8a (slave roller) and the roller 8b (slave roller) are front rollers and are supported between the support member 11b of the front roller support part 11 and the side plate 13.

Notch parts 26 are formed on the upper edges of the support member 11b and the side plate 13.

The roller 8a is supported between he support member 11b and the side plate 13 by inserting the roller shaft 20 in the notch parts 26.

Also, notch parts 27 are formed in the lower edges of the support member 11 and the side plate 13.

The roller 8b is supported between the support member 11b and the side plate 13 by inserting the roller shaft 20 in the notch parts 27.

The rollers 8a and 8b can be easily detached by pulling out the roller shaft 20 from the notch parts 26 and 27.

Thus, the rollers 8a and 8b are freely attachable to and detachable from the front roller support part 11.

Among the rollers 8, the roller 8c (slave roller) and the roller 8d (drive roller) are rear rollers and are supported between the support member 12b of the rear roller support part 12 and the support member 12c.

Notch parts 28 are formed in the lower edges of the support members 12b and 12c.

The roller 8c is supported between the support member 12b and 12c by inserting the roller shaft 20 in the notch parts 28.

The roller 8c can be easily detached by pulling out the roller shaft 20 from the notch parts 28.

Thus, the roller 8c is freely detachable from and attachable to the rear roller support part 12.

Support parts 29 for supporting the bearing parts 22 of the roller 8d (drive roller) and end parts of the fixing shaft 23 are formed at the upper edges of the support member 12b and 2c.

Although these support parts 29 may be formed so as to mount the bearing parts 22 and both ends parts of the fixing shaft 23, the support parts need only be formed as a support part 29a which positions and mounts an end part of the fixing shaft 23 in the side opposite to the connection part 24, at least in the support member 12c.

Further, the support member 12c is provided with a fixing mechanism 30, such as a catch clip or the like, for engaging and fixing an end part of the fixing shaft 23 mounted on a support concave part 29a.

With respect to the roller 8d, an end part of the fixing shaft 23 is positioned by and mounted on the support concave part 29a, and the same one end part is fixed by the fixing mechanism 30, to be supported between the support member 12b and the support member 12c.

The roller 8d can be easily detached by releasing the engagement of the fixing shaft 23 with the fixing mechanism 30 and by releasing the end parts of the rotation shaft 21 from connection with the output shaft side of the motor unit 9.

The roller 8d is thus freely detachable from and attachable to the rear roller support part 12.

The rollers 8 (8a, 8b, 8c, and 8d) supported on the front roller support part 11 and the rear roller support part 12 are supported in parallel with each other.

Also, the rollers 8a and 8b (front rollers) supported on the front roller support part 11 are arranged such that the roller 8a situated in the upper side is positioned in the front side and the roller 8b situated in the lower side is positioned in the rear side.

Also, the rollers 8c and 8d (rear rollers) supported on the rear roller support part 12 are arranged such that the roller 8d situated in the upper side is positioned in the rear side and the roller 8c situated in the lower side is positioned in the front side.

Further, the upper circumferential surfaces of the rollers 8a and 8d situated in the upper side are positioned in the substantial same plane or upper port as those of the upper surface 6a of the metal box, and the support plates 11d and 12d provided in the front and rear roller support parts 11 and 12.

Meanwhile, the motor unit 9 is fixed to the side of the casing 5 forming part of the X-ray foreign-body detector.

This motor unit 9 is formed of a drive motor and a decelerator.

As shown in FIG. 1, a connection part 31 connected with the connection part 24 of the roller 8d forming a drive roller to position the rotation shaft 21 and the output shaft to be coaxial with each other is provided in the side of the output shaft of the motor unit 9.

Also, the other one of paired male and female couplings 24 connected with the side of the end part of the rotation shaft 21 of the roller 8d is fixed to the output shaft of the motor unit 9.

Further, the connection part 24 of the roller 8d and the connection part 31 of the motor unit 9 are connected with each other, so that the rotation shaft 21 of the roller 8d and the output shaft of the motor unit 9 are arranged at positions coaxial with each other. In this state, the paired male and female couplings 25 are connected with each other.

In this manner, rotation of the output shaft of the motor unit 9 is transmitted to the rotation shaft 21.

In addition, the connection between the connection part 24 of the roller 8d and the connection part 31 of the motor unit 9 functions to arrange the rotation shaft 21 and the output shaft at positions coaxial to each other and also functions to set the position of the roller 8d.

That is, with respect to the roller 8d, an end part of the fixing shaft 23 fixing the bearing parts 22 is positioned and fixed in the side of the support member 12c of the rear roller support part 12. The connection part 24 in the opposite side and the connection part 31 of the motor unit 9 are connected with each other and are thereby positioned and supported between the support members 12b and 12c.

Although the motor unit 9 is fixed in the side of the casing 5 forming part of the body of the x-ray foreign-body detector, it may alternatively be fixed to the support member 12b or the metal box 6.

The conveyor belt 10 is a belt member and is tensioned around the rollers 8a, 8b, 8c, and 8d such that the belt surrounds the metal box 6 in the longitudinal direction (in the direction perpendicular to the lateral direction of the slit 7).

When the side plate 13 of the front roller support part 11 is attached to the metal box 6, the conveyor belt 10 is tensioned around the rollers 8a, 8b, 8c, and 8d by a slide with the fixing mechanism 18 engaged with the hook 17.

In addition, the support member 11b and the notch parts 27 of the side plate 13, which support the roller 8b, are provided with an adjustable tension mechanism (not shown) for moving the roller 8b along the notch parts 27, so that the tension of the tensioned conveyor belt 10 can be adjusted.

Thus, the conveyor belt 10 tensioned around the rollers 8a, 8b, 8c, and 8d is supported on the upper surface 6a of the metal box 6 and the support plates 11d and 12d which construct a plane situated at the same level as the upper surface 6a.

This conveyor belt 10 can be easily detached since the tension around the rollers 8a, 8b, 8c, and 8d is relaxed by merely releasing the engagement between the fixing mechanism 18 and the hook 17 related to the side plate 13.

The conveyor belt put on the rollers 8a, 8b, 8c, and 8d can thus be freely detached.

As shown in FIG. 1, the structure of the metal box 6 containing the X-ray detection part 2 and the conveyor part 3 attached to the metal box 6 is covered so as to prevent leakage of X-rays by front, rear, and main covers 32 provided at a lower part of the casing 5.

In addition, openings 33 are formed in the covers 32 over the rollers 8a and 8d and the upper sides thereof, thereby allowing an inspection object to pass through.

In the conveyor part 3 constructed in the above structure, the roller 8d rotates, thereby rotating the conveyor belt 10, which is tensioned around the rollers 8a, 8b, 8c, and 8d, circularly in one direction.

The circular rotating direction of the conveyor belt 10 is the longitudinal direction (front-rear direction) perpendicular to the slit 7 of the metal box 6 which receives the X-rays radiated in a planar form.

Also, the conveyor belt 10 rotates circularly along the upper surface 6a of the metal box 6, and the support plates 11d and 12d.

In this manner, the object to be inspected, which is fed onto the conveyor belt 10, passes through the planar X-rays radiated from the X-ray generation part 1 to the X-ray detection part 2, supported on the upper surface 6a of the metal box 6 and the support plates 11d and 12d as supporting surfaces.

Thus, the structure of the conveyor part 3 is integrated with the metal box 6 as the base member containing the X-ray detection part 2 for detecting the X-rays.

Further, the X-ray detection part 2 and the conveyor part 3 thus integrated construct an X-ray detection unit 100 which conveys an object to be inspected and also detects the X-rays transmitted through.

Accordingly, in the X-ray foreign-body detector, the X-ray detection part 2 is contained in the metal box 6 and the structure of the conveyor part 3 is detachably attached to the metal box 6.

In this manner, the X-ray detection part 2 and the conveyor part 3 which are positioned close to each other to detect a foreign body contained in the object being conveyed are constructed as an independent assembly which is detachable and attachable through the metal box 6. Therefore, maintenance inspections, repairing, cleaning, and the like, can be easily carried out on respective parts.

This metal box 6 forms a waterproof structure throughout the entire circumference and is structured such that the X-rays which pass through the slit 7 are received by the X-ray detection part 2. Therefore, the X-ray detection part 2 is shielded against moisture which leaks from the object to be inspected during conveyance, and dirty thereof can be water-washed.

In the metal box 6, the flattened upper surface 6a serves as a support surface which supports the conveyor bet 10 on which the object to be inspected is mounted. Accordingly, no extra support plate or the like is required, so that the structure is simplified. It is therefore possible to reduce gaps and joints where miscellaneous germs easily appear.

In addition, the rollers 8, the front roller support part 11, and the rear roller support part 12 are detachable and attachable. When they are detached, no gaps or joints exist any more and only the outer circumference of the metal box 6 are exposed so that cleaning is facilitated and sanitary improvements are achieved.

In addition, the structure of the X-ray detection part 2 and the conveyor part 3 is constructed into an integrated X-ray detection unit, so that this X-ray detection unit and the x-ray generation part 1 can be manufactured on separate manufacture lines. Therefore, productivity can be improved and manufacture costs can be reduced.

Since this X-ray detection unit itself functions to convey an object to be inspected and to detect the X-rays transmitted through the object, it can be used variously, not only for that determined by an X-ray foreign-body detector, but also any structure comprising the X-ray generation part 1.

Figure 4:
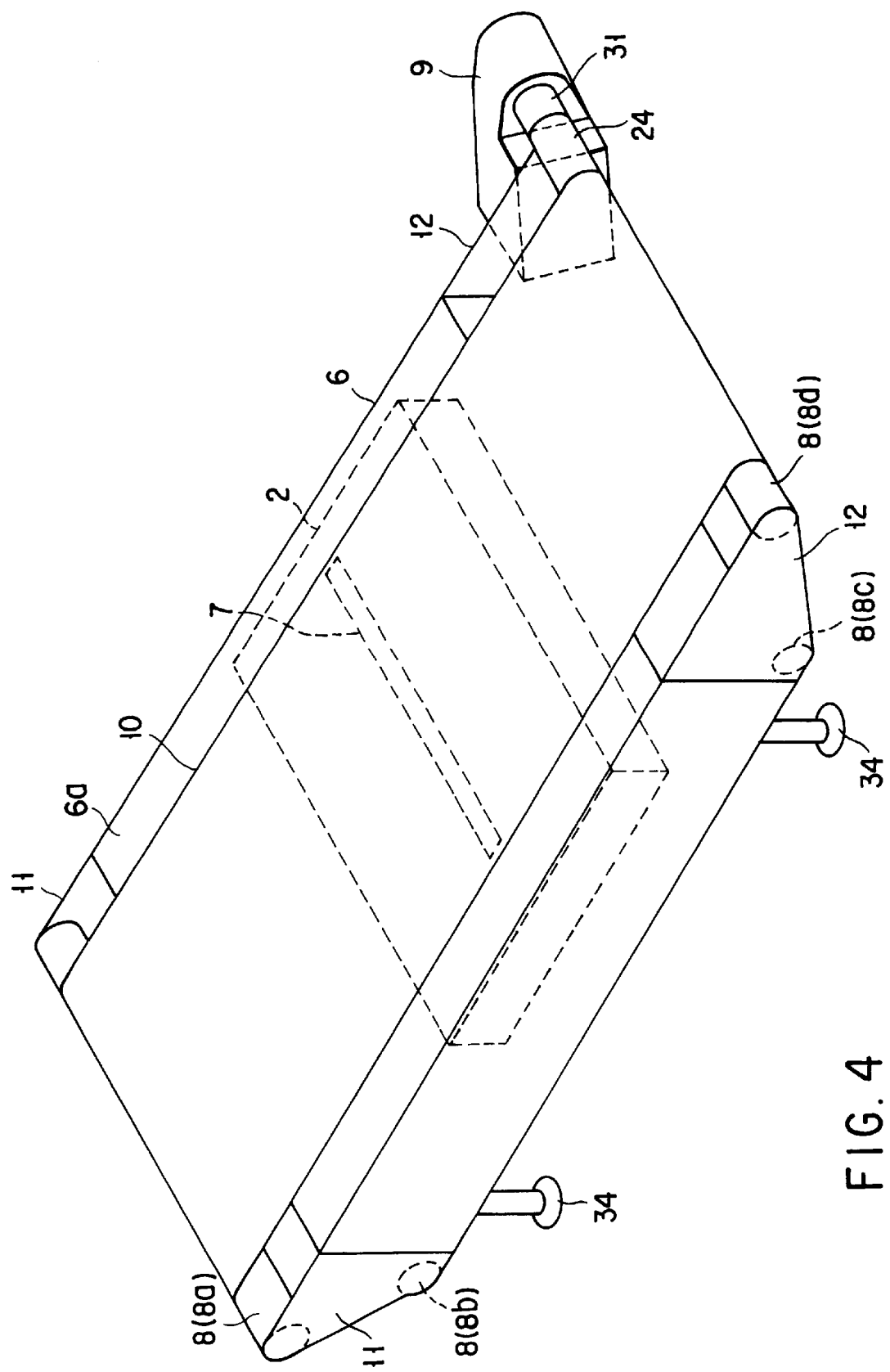
FIG. 4 is a perspective view showing a structure in which legs are provided for the X-ray detection unit shown in FIG. 2.

Particularly with respect to attachment and mounting of the X-ray detection unit, the mode of usage is not limited to one, e.g., the metal box 6 may be attached in another position, or may be set with legs 34, as shown in FIG. 4.

In case where four legs (only two of which are shown in FIG. 4) are provided at four corners on the lower part of the metal box 5, as shown in FIG. 4, it is desirable to fix the motor unit 9 to the support member 12b or metal box 6.

Alternatively, it is possible to arrange the motor unit 9 inside the metal box 6.

In the first embodiment described above, the front rollers consist of rollers 8a and 8b, and the rear rollers consist of rollers 8c and 8d.

Therefore, at least each one of the front and rear rollers may be provided.

As explained above, in the first embodiment of the X-ray foreign-body detector according to the present invention, an X-ray detection part is contained and mounted inside the metal box of a X-ray detection unit, and an integrated X-ray detection unit in which a conveyor belt and front and rear rollers on which the conveyor belt hangs, are freely detachable and attachable, is used for the metal box.

Since the structure of the X-ray detection part and the conveyor system is thus integrated into an X-ray detection unit, this unit itself has a function of conveying an object to be inspected and also a function of detecting an X-ray which has passed through the object. Therefore, the detection unit can be variously used, not only for one determined by the X-ray foreign-body detector but also for other structures generating X-rays.

In addition, the structure of the conveyor system (front and rear rollers) is detachably attached. Therefore, the X-ray detection part and conveyor part positioned close to each other are constructed into an independent assembly through the metal box, in order to detect a foreign body contained in the object being conveyed. Accordingly, maintenance inspections, repairs, cleaning, and the like can be easily carried out.

Since the metal box is arranged so as to support the conveyor belt with an inspection object set on the upper surface of the metal box, no extra support plate is required, so that the structure is simplified and it is possible to reduce gaps and joints where germs may easily linger.

In addition, if the front and rear rollers and the conveyor belt are detached, no gaps or joints exist and the outer circumference of the metal box is exposed, so that cleaning is easy and sanitary improvements are achieved.

As described above, the X-ray foreign-body detector according to the present invention uses an integrated X-ray detection unit in which an X-ray detection part is contained and mounted in a metal box and front and rear rollers around which a conveyor belt is put on are detachable from and attachable to the metal box.

In this manner, it is possible to obtain effects of the X-ray detection unit described above and also to manufacture the x-ray detection unit and an X-ray generation part for generating X-rays in different manufacture lines. Accordingly, productivity can be improved and manufacturing costs can be reduced.

(Second Embodiment)

Figure 5:
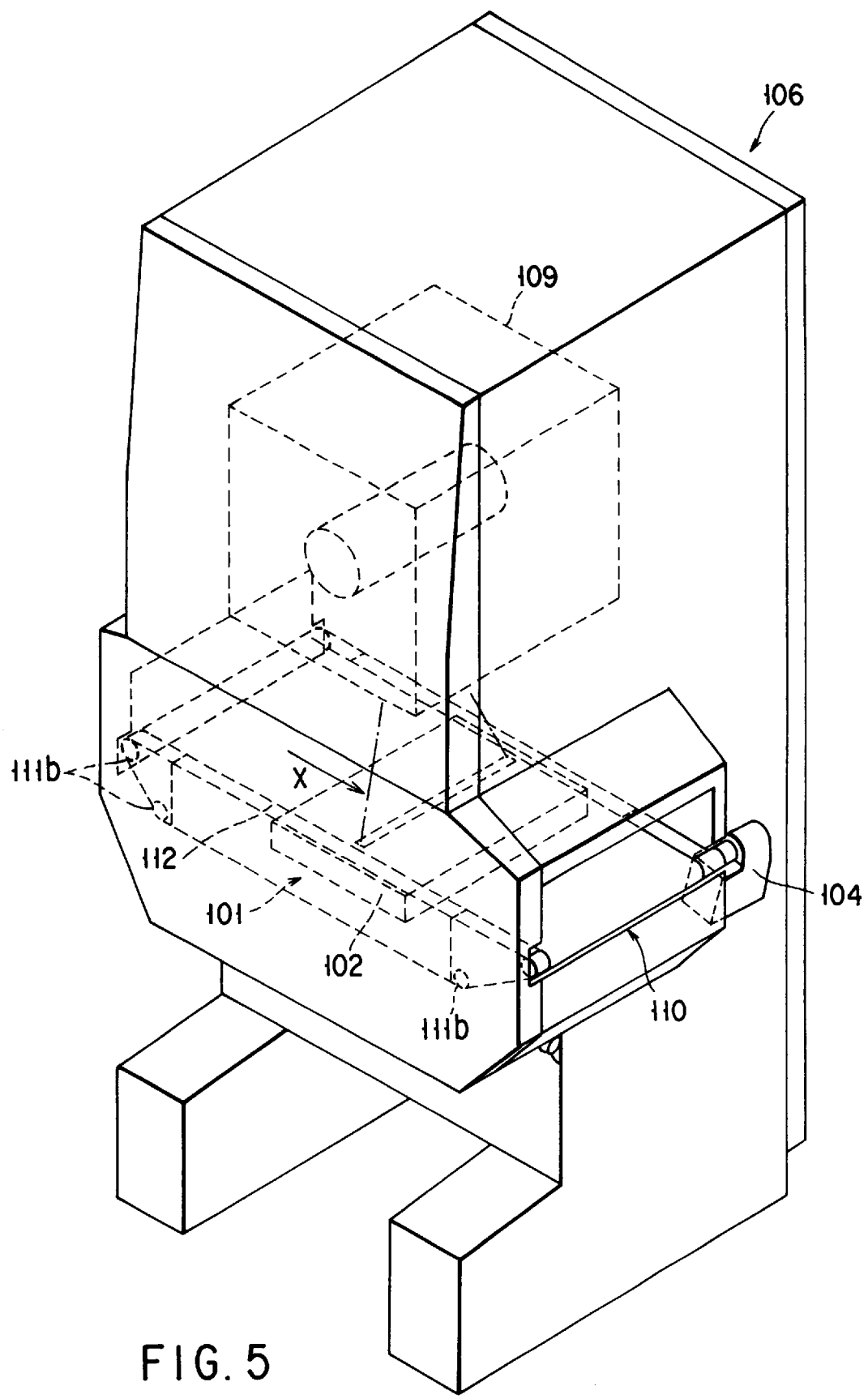
FIG. 5 is a perspective view showing the entire structure of the second embodiment of the X-ray foreign-body detector according to the present invention.

FIG. 5 shows the entire structure of the second embodiment of an X-ray foreign-body detector according to the present invention.

As shown in FIG. 5, in the x-ray foreign-body detector 106 according to the second embodiment, a conveyor 101 is provided at the substantial center part, and an X-ray generation part is provided at an upper part.

Further, in this X-ray foreign-body detector 106, a foreign body contained in an object to be inspected can be detected by an x-ray detection part, by radiating X-rays from the X-ray generation part 109 while conveying and driving the conveyor belt 112 of the conveyor 101 in the X-direction.

Figure 6:
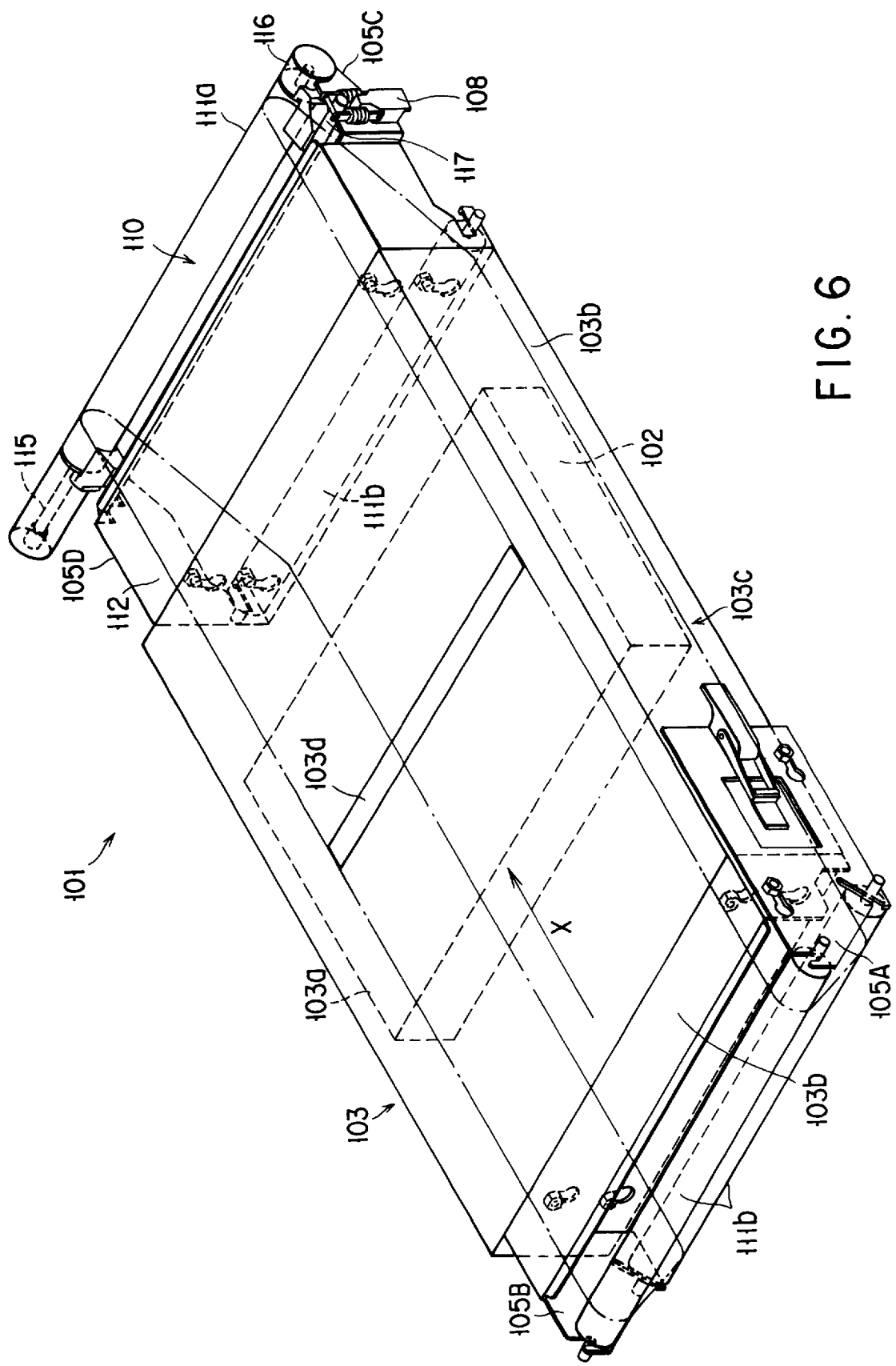
FIG. 6 is a perspective view showing a conveyor part shown in FIG. 5.

FIG. 6 shows the entire structure of the conveyor 101.

The conveyor 101 has a unit structure as shown in FIG. 6.

This unit is constructed by including the following parts in a metal box 103 as an X-ray detection container.

The metal box 103 is formed by bending a body (metal plate or the like) which does not leak X-rays. The upper surface of the metal box 103 is a horizontal receiving base 103a, and the entire circumference of the metal box is sealed with four side surfaces 103b and bottom surface 103c.

This conveyor 101 conveys the object to be inspected, along the lengthwise direction (X-direction) in FIG. 6.

Also, in the metal box 103, support plates 105 (105A, 105B, . . . , 105D) are respectively formed and projected at both of the front and rear ends of the object in the conveying direction.

Two slave rollers 111b are provided between the support plates 105A and 105B in the front side viewed from the conveying direction X, and a drive roller 111a and a slave roller 111b are provided between the support plates 105C and 105D in the rear side.

Between the drive roller 111a and the slave roller 111b, a conveyor belt 112 is tensioned along the X-direction.

Further, the conveyor belt 112 is conveyed and driven by rotation of a motor unit 104 (shown in FIG. 5) connected with the drive roller 111a. Each slave roller 111b supports and guides conveyance of the conveyor belt 112.

In addition, an X-ray detection part 102 is provided in the metal box 103.

The X-ray detection part 102 detects incident X-rays which enter through an opening part 103d opened in the receiving base 102a.

This opening part 103d is closed by a plate which transmits the X-ray.

That is, the object to be inspected, which is conveyed in the X-direction on the conveyor belt 112, is exposed to the X-ray from the X-ray generation part 109 at the upper part, when the object passes over the opening part 103d. Since the X-rays thus penetrate through the object to be inspected, foreign bodies inside the object can be detected by the X-ray detection part 102.

The conveyor 101 constructed in the structure described above has a flat conveyor surface and is capable of detecting foreign body using X-rays while stably conveying an object to be inspected.

Also, a drive roller 111a and a slave roller 111b are spaced further apart, in the conveying direction, than the lower two slave rollers 111b.

Therefore, the wound form of the conveyor belt 112 is similar to an upside-down trapezoid.

In this manner, only the portion where the object is received from a device in the front stage and the portion where the object is delivered to a device in the rear stage are projected most in the conveying direction, so that stable receipt and delivery can be achieved by the conveyor belt 112 of the conveyor 102.

In addition, the structure is arranged so as to contain the X-ray detection part 102 inside the metal box 103 of the conveyor 101. If X-rays leak from the X-ray detection part 102, they can be prevented from leaking by the metal box 103.

Figure 7:
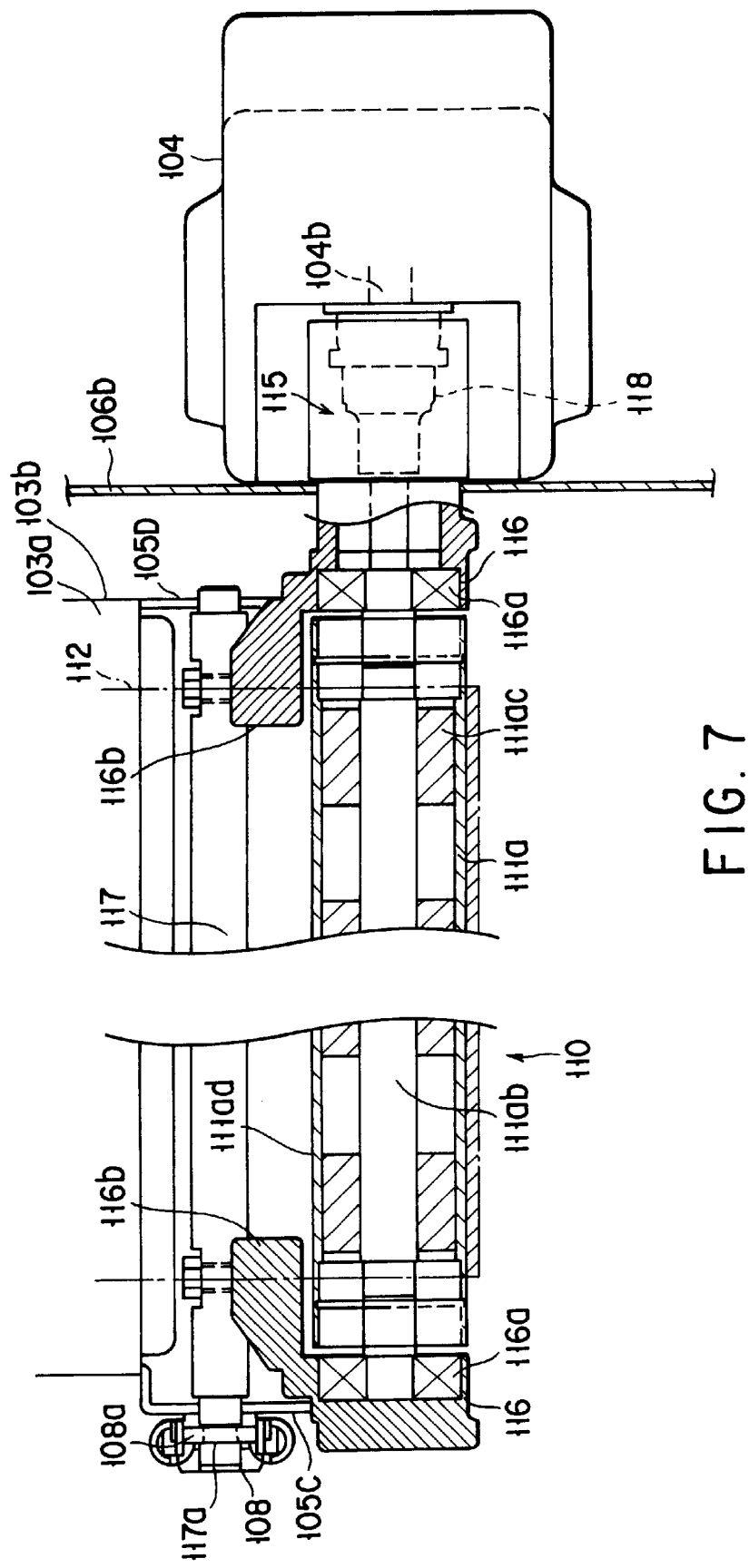
FIG. 7 is a plane cross-sectional view showing a drive roller unit shown in FIG. 5.
Figure 8:
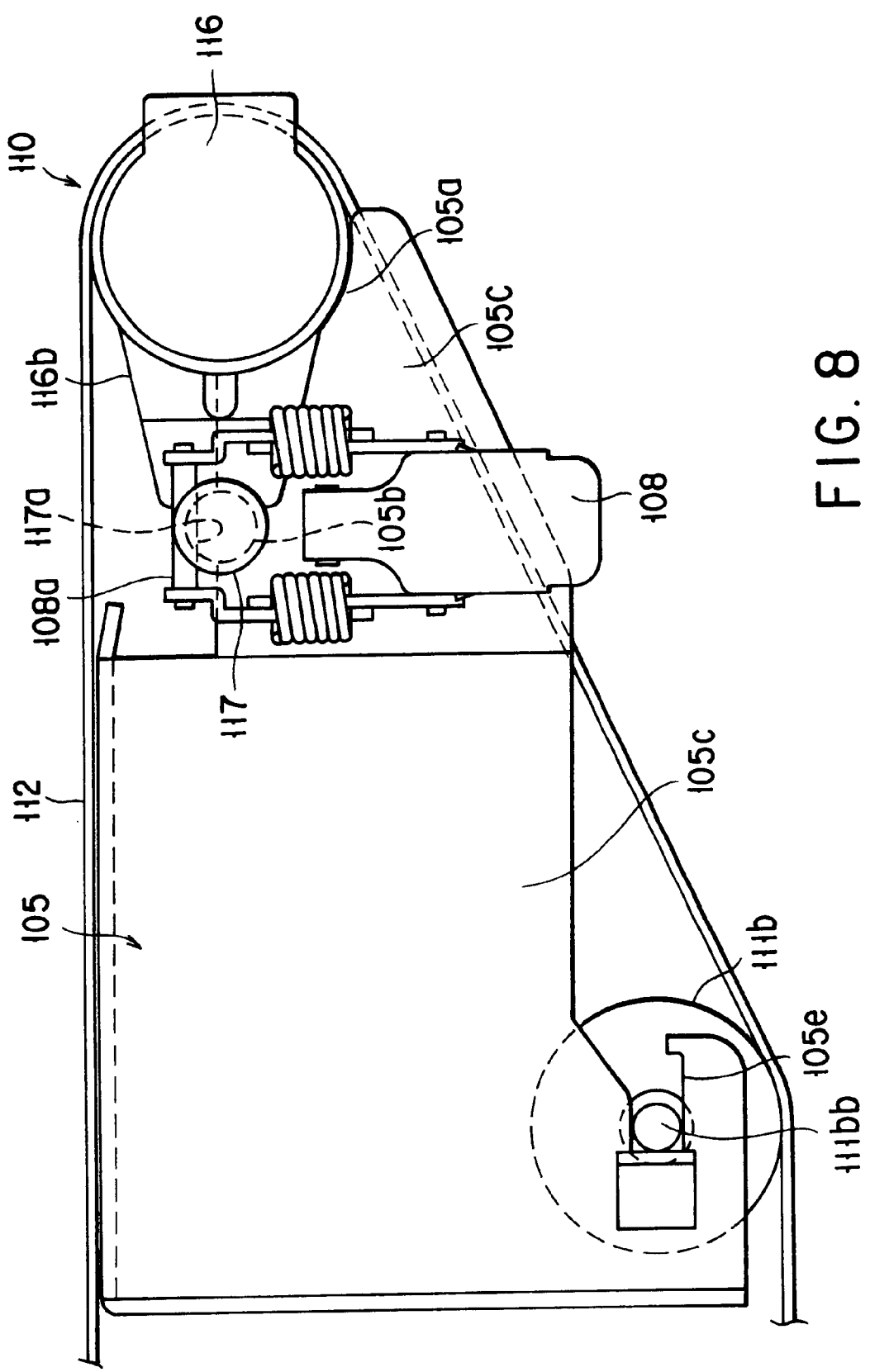
FIG. 8 is a front view showing the drive roller unit shown in FIG. 5.

FIGS. 7 and 8 are partially enlarged views of the drive roller unit 110 of the conveyor 101.

As shown in FIGS. 7 and 8, bearing parts 116 are respectively arranged at both ends of the drive roller 111a.

Bearings 116a which rotatably support a rotation shaft 111ab are provided in these bearing parts 116.

The rotation shaft 111ab is fixed to and supported on the outer circumferential part 111ad of the drive roller 111a by support parts lilac provided at a plurality of portions inside the drive roller 111a.

This drive roller 111a is arranged such that the upper circumferential surface is set at the substantial same or more height as the upper surface of the receiving base 103a.

Projecting parts 116b facing the conveying direction are respectively formed on the paired bearing parts 116 and are fixed to one fixing shaft 117 in parallel the rotation shaft 111ab, by screws.

The drive roller 111a, bearing parts 116, and fixing shaft 117 form an integrated drive roller unit 110.

In addition, engaging grooves 105a and 105b matched with the outer shapes of the bearing parts 116 and fixing shaft 117 are formed in the support plates 105C and 105D, so that the drive roller unit 110 is positioned at an end part position of the support plate 105.

The metal box 103 of the conveyor 101 has one side surface 103b fixed like a cantilever.

The support plate 105C facing the front surface side of the X-ray foreign-body detector 106 is provided with a fixing mechanism 8 such as a catch clip or the like for fixing the fixing shaft 117.

An engaging member 108a of the fixing mechanism 108 is engaged in the engaging grooves 117a of the fixing shaft 117, so that the drive roller unit 110 can be fixed to the support plate 105 in a state positioned as described above.

A motor unit 104 is provided in the side of one side part of the drive roller 111a (an attachment plate 106b provided for the X-ray foreign-body detector 106).

This motor unit 104 is constructed by a drive motor and a decelerator.

The output shaft 104b of the motor unit 104 is provided to be coaxial with the drive roller 111a, and these components are connected by a connection part 115.

The connection part 115 is constructed by paired (male and female) couplings 118 respectively fixed to the output shaft 104b of the motor unit 104 and the rotation shaft 111ab of the drive roller 111a.

Also, as shown in FIG. 8, a slave roller 111b is provided obliquely below the drive roller 111a.

This slave roller 111b is engaged and held in hold grooves 105 of paired support plates 105C and 105D.

Although not shown in the figures, a shaft 111bb is fixed and the outer circumferential surface thereof is arranged rotatable through bearings provided inside the slave roller 111b.

Figure 9:
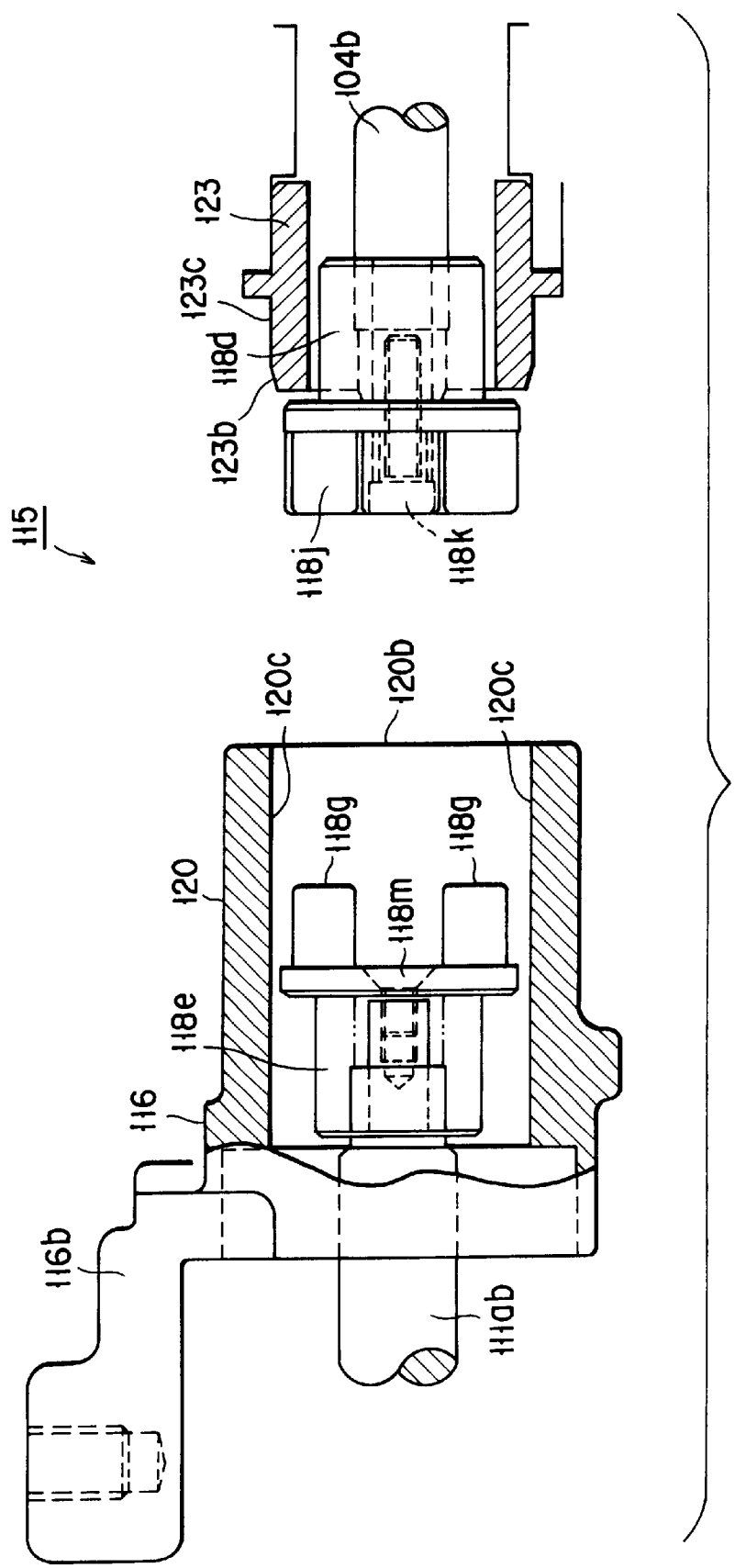
FIG. 9 is a plane cross-sectional view showing a connection part shown in FIG. 6.

FIG. 9 is a flat cross-sectional view showing a connection part 15.

Figure 10A:
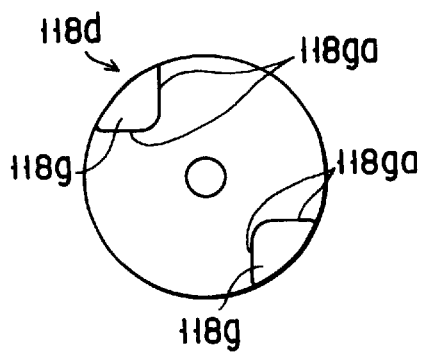
FIGS. 10A, 10B, 10C, and 10D are views showing the structure of couplings shown in FIG. 6.
Figure 10B:
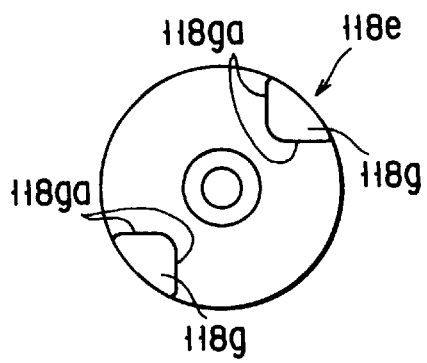

FIGS. 10A and 10B are side views respectively showing the couplings.

Figure 10C:
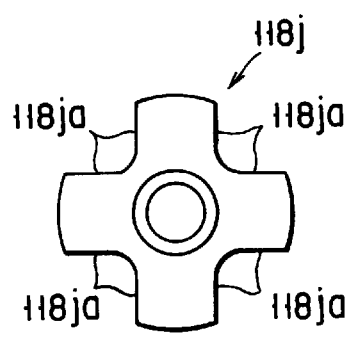

FIG. 10C is a side view of an intermediate disk.

Figure 10D:
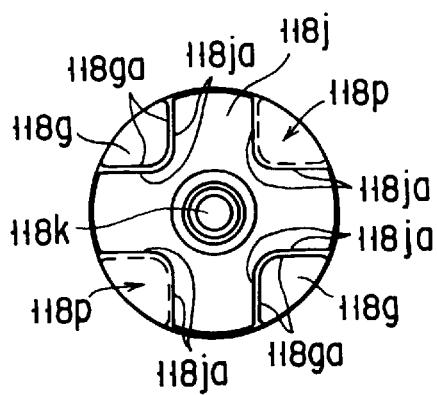

FIG. 10D is a side view showing a state where an intermediate disk is attached to one of the couplings.

The output shaft 104b and the rotation shaft 111ab of the drive roller 111a can be connected freely by the couplings.

The couplings 118 are constructed by a coupling 118d in the side close to the motor unit 104 and a coupling 118a in the side close to the drive roller 111a, which have substantially the same structure as each other.

Further, these couplings 118e are contained inside a cylindrical protection cover 120.

This protection cover 120 is formed to be continuous along the axial direction of the bearing parts 116 and is long enough to contain 118d and 118e, and has a predetermined inner diameter.

The inner circumference of the top end part 120b of the protection cover 120 is formed in a tapered shape.

Explanation will now be made of the motor unit 104 and the connection part 115. A receiving seat (protection cover) 123 is projected and fixed to be coaxial with the part of the output shaft 104b.

This receiving seat 123 has a substantially columnar shape having a predetermined outer diameter, and the top end part 23b is formed in a tapered shape.

The inner circumferential surface 120c of the protection cover 120 and the outer circumferential surface 123c of the receiving seat 123 are engaged with each other with predetermined precision. The axial centers of the couplings 118d and 118e are positioned uniformly.

Further, the coupling 118d is fixed, together with the intermediate disk 118j, to an output shaft 104b by a bolt 118k.

Engaging projections 118g are formed and projected at two portions on the circumferential surface of each of the couplings 118d and 118e with the rotation center situated as the center.

The intermediate disk 118j is formed in a substantial cross shape having a predetermined width, as shown in FIG. 10C.

This intermediate disk 118j is made of a resin such as ultra-high molecular polyethylene, MC nylon, polyacetal, or the like, and has excellent strength, excellent self-lubrication characteristics, excellent friction resistance, excellent heat resistance, excellent formability, and low water absorbency.

With respect to this intermediate disk 118j, junction edges 118j a contact slanting edges 118ga of one coupling with a predetermined allowance, as shown in FIG. 10D.

In this state, the engaging projections 118g of the coupling 118e are engaged with the engaging part 118p, which is opened in the side of the coupling 118d.

In this manner, the output shaft 104b of the motor unit 104 and the rotation shaft 111ab of the drive roller 111a can be connected with and disconnected from each other.

If there is an offset or declination between the output shaft 104b of the motor unit 104 and the axial center of the rotation shaft 111ab of the drive roller 111a, such an offset or declination can be absorbed by using the couplings 118d and 118e described above.

In addition, the couplings 118d and 118e do not directly contact each other but are connected through an intermediate disk 118j. Therefore, there is no junction portion between metal parts.

Specifically, the slanting edges 119ga of the couplings 118d and 118e and the junction edges 118ja of the intermediate disk 118j construct a junction between metal and resins, so that friction therebetween can be reduced to a minimum.

In this manner, it is possible to achieve low noise, low vibration, and long lifetime of the connection part 118.

Further, if the axial centers of the output shaft 104b of the motor unit 104 and the rotation shaft 111ab of the drive roller 111a are shifted from each other, wear and twist of the rotation shaft 111ab can be prevented.

It is also possible to prevent one of the output shaft 104b and the rotation shaft 111ab from causing the other one to warp or bend.

Meanwhile, the resin side of the intermediate disk 118j will become worn with use due to friction at the junction between the couplings 118d and 118e.

However, the disk can be replaced with a new intermediate disk by a simple operation of detaching and attaching the bolt 118k.

Figure 11:
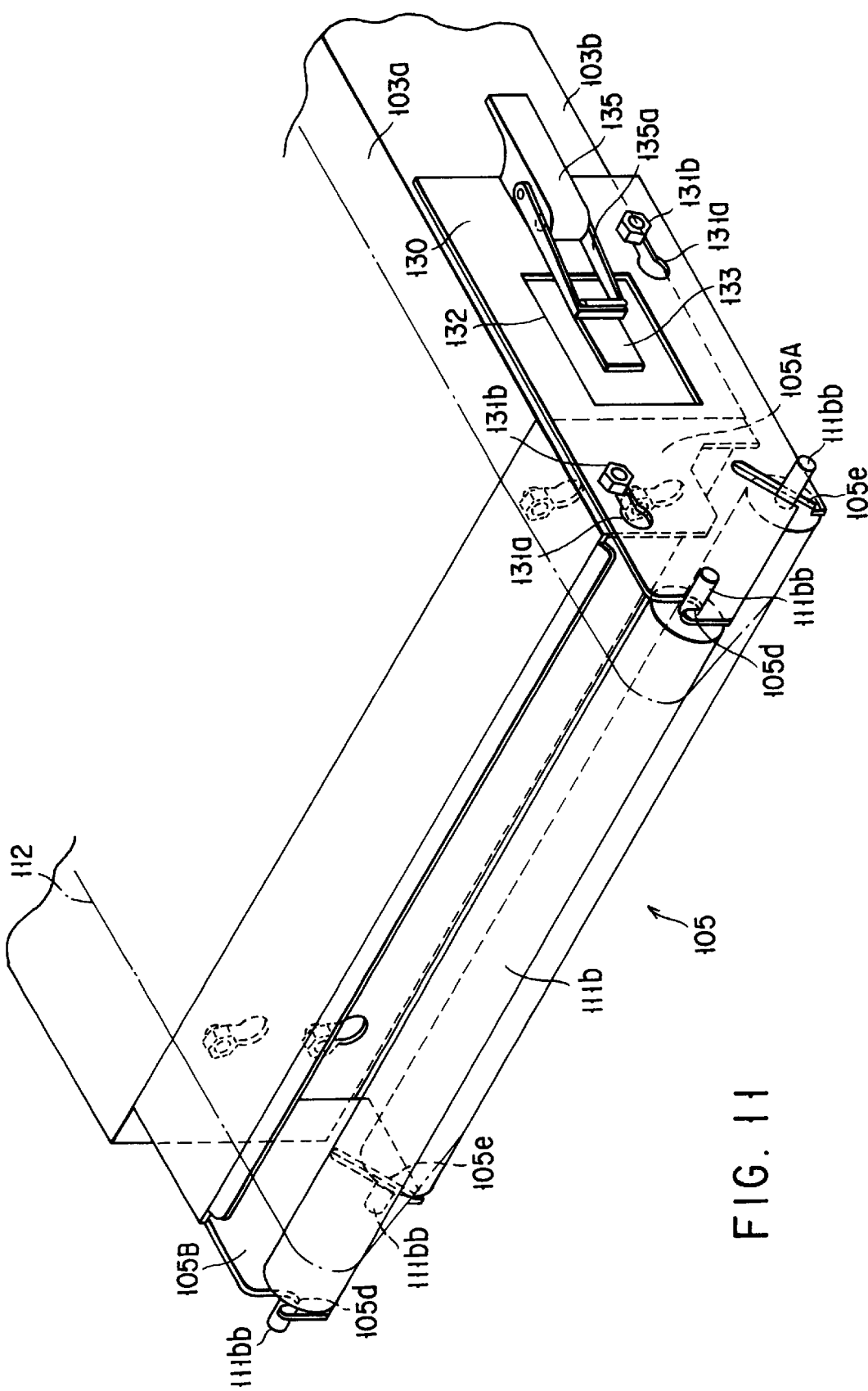
FIG. 11 is a perspective view showing the structure of a slave roller part shown in FIG. 6.

FIG. 11 is a partial perspective view of the slave roller 111b of the conveyor 101.

Figure 12:
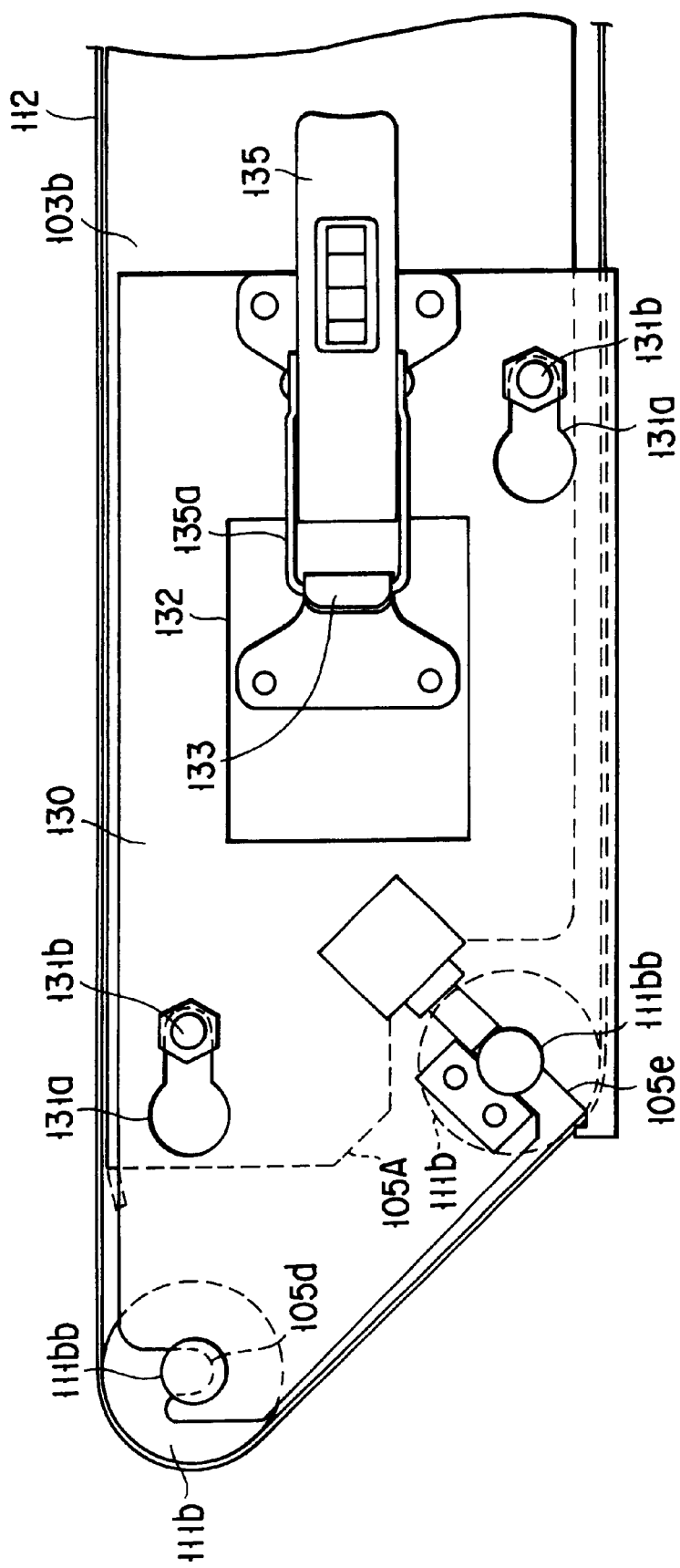
FIG. 12 is a front view showing the structure of a slave roller part shown in FIG. 6.

In addition, FIG. 12 is a partial front view of the slave roller 111b of the conveyor 101.

As shown in FIGS. 11 and 12, two slave rollers 111b are arranged vertically between the slide plate 130 and the support plate 105B.

The shaft 111bb is engaged and held in the hold grooves 105d and 105e of the support plate 105B and the slide plate 130.

Although not shown in the figures, the shaft 111b is fixed and the outer circumferential surface thereof is arranged to be rotatable through the bearings provided inside the slave roller 111b.

One of the support plates 105 (in the front surface side of the X-ray foreign-body detector 106) is provided with a slide plate 130.

A plurality of (two) holes 131a each including a small-diameter part and a large diameter part continuous to each other are provided in the slide plate 130.

In this respect, engaging parts 131b respectively comprised of collars engaged in the small-diameter parts of the holes 131a of the slide plate 130, bolts inserted in the large-diameter parts, and washers are provided on the side surface 103b of the metal box 103.

Specifically, the slide plate 130 hangs on the side surface 103b of the metal box 103 by engaging the holes 131a with the bolts and washers of the engaging parts 131b and by engaging them with the collars of the engaging parts 131b.

Also, the slide plate 130 is provided with a fixing mechanism 135 such as a catch clip or the like engaged with a hook 133 provided on the side surface 103b of the metal box 103.

When the slide plate 130 is set on the side surface 103b of the metal box 103, the hook 133 is exposed from an opening hole 132.

An engaging member 135a of the fixing mechanism 135 is engaged with the hook 133.

By thus engaging the fixing mechanism 135 with the hook 133, the slide plate 130 slides such that the small-diameter parts of the holes 131a are engaged with the collars of the engaging parts 131b.

In addition, it can be easily detached from the side surface 103b of the metal box 103 by releasing the engagement of the fixing mechanism 135 with the hook 133 and by detaching bolts and washes of the engaging parts 131b from the holes 131a.

In this manner, the support port of the slave roller 111b is constructed by the slide plate 130 attached to the side surface 103b of the metal box 103 together with the support plate 105B hanged to the front surface of the metal box 103. Further, the slide plate 130 may be independently provided to the metal box 103 or the support plate 105.

By the structure as described above, the slide plate 130 slides in relation to the metal box 103, as the engaging member 135a of the fixing tool 135 is engaged with the hook 133.

This sliding direction is the direction in which a pair of slave rollers 111b are slid in the outward direction along the conveying direction.

In this manner, the conveyor belt 112 is pushed out from inside so that a predetermined tension is applied to the conveyor belt 112.

In the conveyor 101 having the structure as described above, the rotation of the drive motor is decelerated by a decelerator, thereby rotating the output shaft 104b.

This output shaft 104b is connected with the rotation shaft 111ab of the drive roller 111a of the conveyor unit through the couplings 118 of the connection part 115.

In this manner, the drive roller 111a is rotated so that the conveyor belt 112 tensioned around the drive roller 111a and the slave roller 111b moves in one direction.

Further, the X-ray generation part 109 radiates X-rays onto an object to be inspected, with the object mounted and moved on the conveyor belt 112.

In addition, the X-ray detection part 2 detects X-rays which have passed through the object to be inspected and detects foreign bodies contained in the object.

A control part not shown determines whether the object to be inspected is good or not by detection of foreign bodies by means of the X-ray detection part 102, and outputs a selection signal for a defective object.

Next, disassembly of the conveyor 101 based on the structure described above will now be explained.

The conveyor 101 requires to be disassembled for periodical cleaning (sterilization and disinfection) and maintenance.

Disassembly of the conveyor 101 is carried out by firstly moving the slide plate 130.

Figure 13:
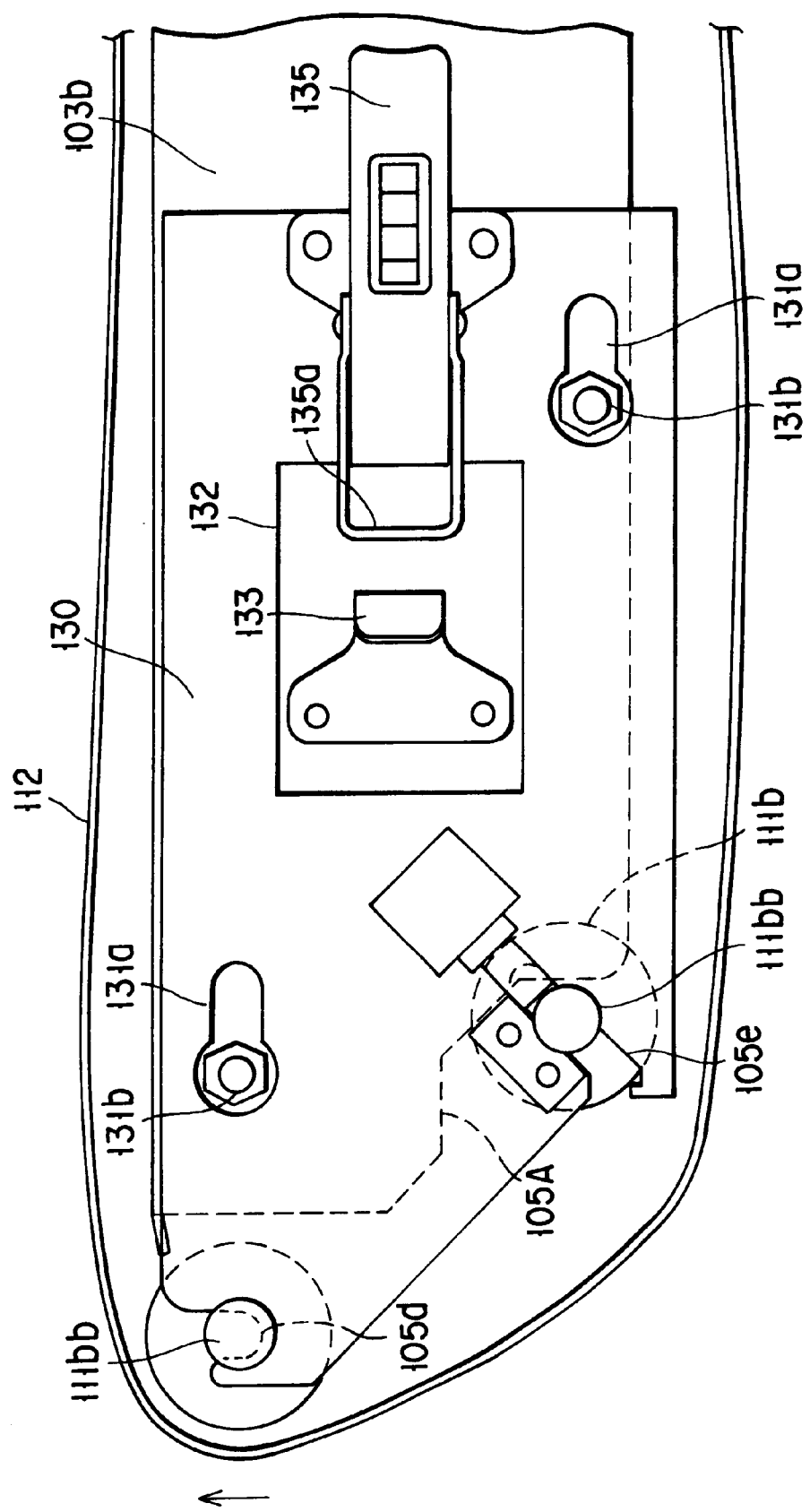
FIG. 13 is a view for explaining operation of detaching a slave roller shown in FIG. 6.

FIG. 13 is a side view showing a moving state of the slide plate 130.

At first, the fixing mechanism 135 provided on the slide plate 130 is released and operated so that the engaging member 135a is released from the hook 133.

In this manner, the slide plate 130 can be moved along the conveying direction.

Further, the slide plate 130 is moved in the direction (the right side in FIG. 13) in which the tension of the conveying belt 112 based on the pair of slave rollers 111b is relaxed.

Concurrently, the slide plate 130 is supported, at the holes 131a at upper and lower two positions, by the engaging parts 131b, so this plate can be prevented from falling off when it slides.

As shown in FIG. 13, the pair of slave rollers 111b and 111b provided in the front side in the conveying direction move to the drive roller 111a and slave roller 111b provided in the rear side in the conveying direction, by sliding the slide plate 130. The diameter of the total circumference defined by the four rollers is reduced to be smaller than that of the conveyor belt 112.

In this manner, the loosened conveyor belt 112 can be removed, from in the front side.

Thereafter, the support plates 105A and 105B, and the shaft 111bb of each of the slave rollers 111b at both ends can be detached from the hold grooves 105d and 105e of the slide plate 130, in the direction indicated by an arrow in FIG. 13.

After the slave roller 111bb is detached, the slide plate 130 is free, so that this plate can be detached with the large-diameter parts of the long grooves 131a adjusted to the screw parts 131b.

Figure 14:
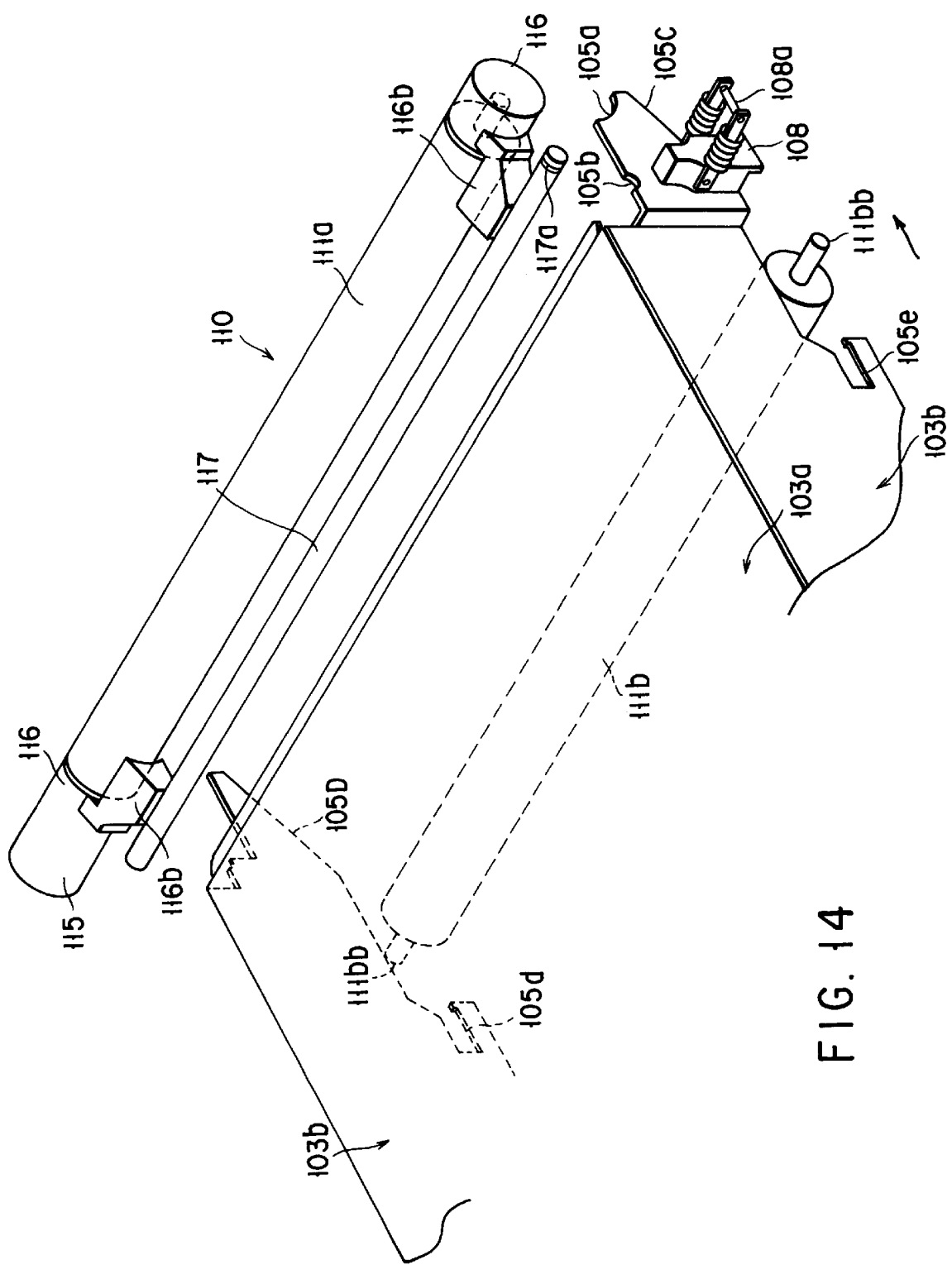
FIG. 14 is a view for explaining operation of detaching the drive roller unit shown in FIG. 5.

Next, as shown in the perspective view of FIG. 14, the drive roller unit 110 and slave roller 111b provided in the rear side in the conveying direction are detached.

With the conveyor belt 112 detached, the fixing mechanism 108 is released, thereby releasing the engagement of the fixing shaft 117 with the engaging grooves 117a provided in the drive roller unit 110.

In this manner, fixing to the support plate 105C in the front side of the device where the fixing mechanism 108 is provided can be released and detached.

As shown in FIG. 9, the deep side of the drive roller unit 110 is positioned by engagement between a protection cover 120 and a receiving seat 123. However, the protection cover 120 can be detached and taken out by taking out the drive roller unit 110 to the front side of the device.

At this time, connection between the output shaft 104b of the motor unit 104 and the rotation shaft 111ab of the drive roller 111a can be released.

Specifically, at the same time the engagement between the protection cover 120 and the receiving seat 123 is released, the engagement between the couplings 118 each other can be released.

Therefore, as shown in FIG. 14, in the drive roller unit 110, the connection part 115 positions and fixes and holds the shaft in the deep side of the device. Therefore, the bearing part 116 provided at this portion does not require support by the support plate 105D.

In the drive roller unit 110, the bearing parts 116 at both ends are fixed by screws to one fixing shaft 117 through extending parts 116b. Therefore, the drive roller unit 110 can be stocked without disassembling itself even when it is detached from the device body.

Thereafter, the shaft 111bb at both ends of the slave roller 111b can be detached, in the direction indicated by an arrow in the figure, from the hold groove 105e of the side surface 103b.

In addition, the drive roller unit 110, three slave rollers 111b, and conveyor belt 112 can be easily attached by reversing the order of the above-described operation.

At this time, the motor unit 104 and the drive roller 111a are connected by the connection part 115.

That is, the axis of the couplings 118a and 118b can correspond to and engage with each other by engaging the receive seat 123 with the protection cover 120.

In this manner, the rotation parts (including couplings 118a and 118b and the like) are not exposed to the outside, so safety is obtained.

In addition, when detaching the conveyor unit 103, the couplings 118a and 118b are covered with the protection cover 120 until the motor unit 104 is detached from the support unit 102. Therefore, the couplings 118 are exposed to the outside after connection is released. Safety can accordingly ensured.

In the above explanation to the second embodiment, the motor unit 104 is not attached to the conveyor 101 but is attached to the x-ray foreign-body detector 106. The structure is not limited hitherto but may be arranged such that the motor unit 104 is attached to the side surface 103b of the casing 103 of the conveyor 101.

Accordingly, in the X-ray foreign-body detector according to the second embodiment of the present invention, the driver roller unit is constructed such that the bearing parts at both end parts of the drive roller are integrated by a fixing shaft, and these components can be integrally detachable from and attachable to the metal box. Therefore, the drive roller can be easily attached and detached so that maintenance and cleaning can be easily carried out.

In addition, in the X-ray foreign-body detector according to the second embodiment of the present invention, the installation position of the drive roller unit can be positioned at a constant position by the structure in which the bearing parts and the fixing shaft are respectively positioned in the engaging grooves provided in the metal box.

Also, in the X-ray foreign-body detector according to the second embodiment of the present invention, the fixing shaft can be constructed such that it can be freely engaged with the fixing shaft with use of a fixing mechanism. Therefore, the drive roller unit can be attached to or detached from the metal box through an easy operation.

In the X-ray foreign-body detector according to the second embodiment of the present invention, the motor and the rotation shaft of the drive roller can be separated freely at a connection part, so that attachment and detachment of the drive roller unit including the drive force transmission route can be facilitated.

Specifically, the structure is arranged such that connection and disconnection can be achieved by the junction coupling. Therefore, the connection at the drive transmission part can be easily released.

In addition, in the X-ray foreign-body detector according to the second embodiment of the present invention, the protection case and receiving seat, which are coaxial with the couplings, are engaged with each other thereby to align axially. Therefore, the connection and positioning with respect to the axial center of the drive roller can be easily carried out at this connection part, so that stable drive-force transmission can be achieved.

Also, in the X-ray foreign-body detector according to the second embodiment of the present invention, an advantage is obtained in that the drive roller unit can be easily attached and detached, as described above, by using the conveyor described above.

In addition, the structure is arranged such that an X-ray detection part is provided in a sealed space formed by a drive roller and three slave rollers in a sealed casing. As a result, leakage of X-rays from the X-ray detection part can be prevented.

Also, in the X-ray foreign-body detector according to the second embodiment of the present invention, the slide plate which supports axially two slave rollers is constructed to be slidable freely toward the side of the drive roller. Therefore, the belt can be replaced with the tension of the belt loosened, and subsequently, the drive roller unit and slave rollers can be detached easily, so that disassembly and cleaning of the conveyor can be carried out easily.

(Third Embodiment)

Next, a modification of changing the device length of the X-ray foreign-body detector will be explained as a third embodiment of the present embodiment invention.

Although the device length of the X-ray foreign-body detector according to the present invention is determined by the length of the conveying distance of the conveyor part, the conveying length of the conveyor part can be easily changed by the conveyor part which is incorporated, together with an X-ray detection part, into a unit as an X-ray detection unit.

Figure 15:
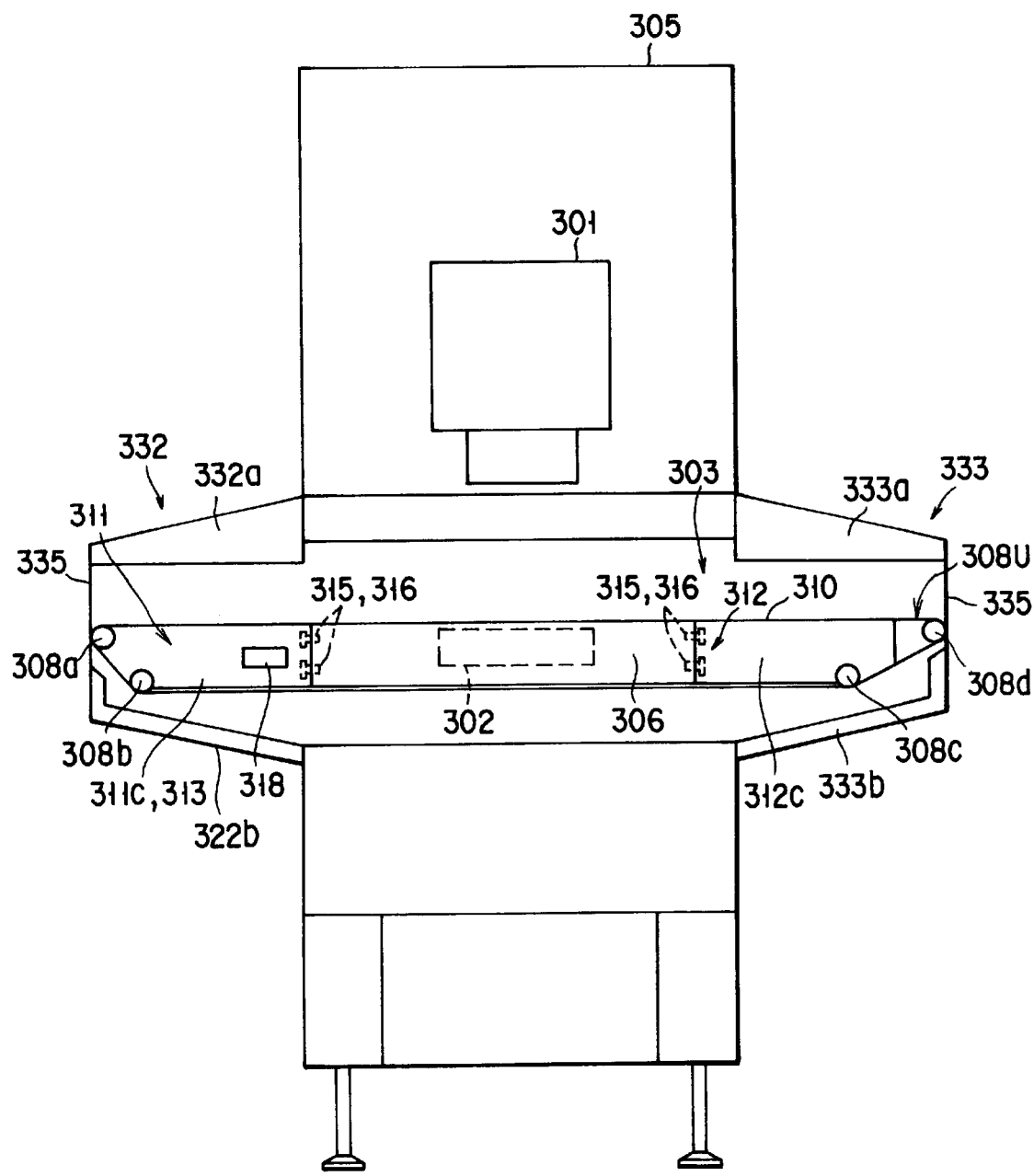
FIG. 15 is a front view showing the entire structure of the third embodiment of the X-ray foreign-body detector according to the present invention.
Figure 16A:
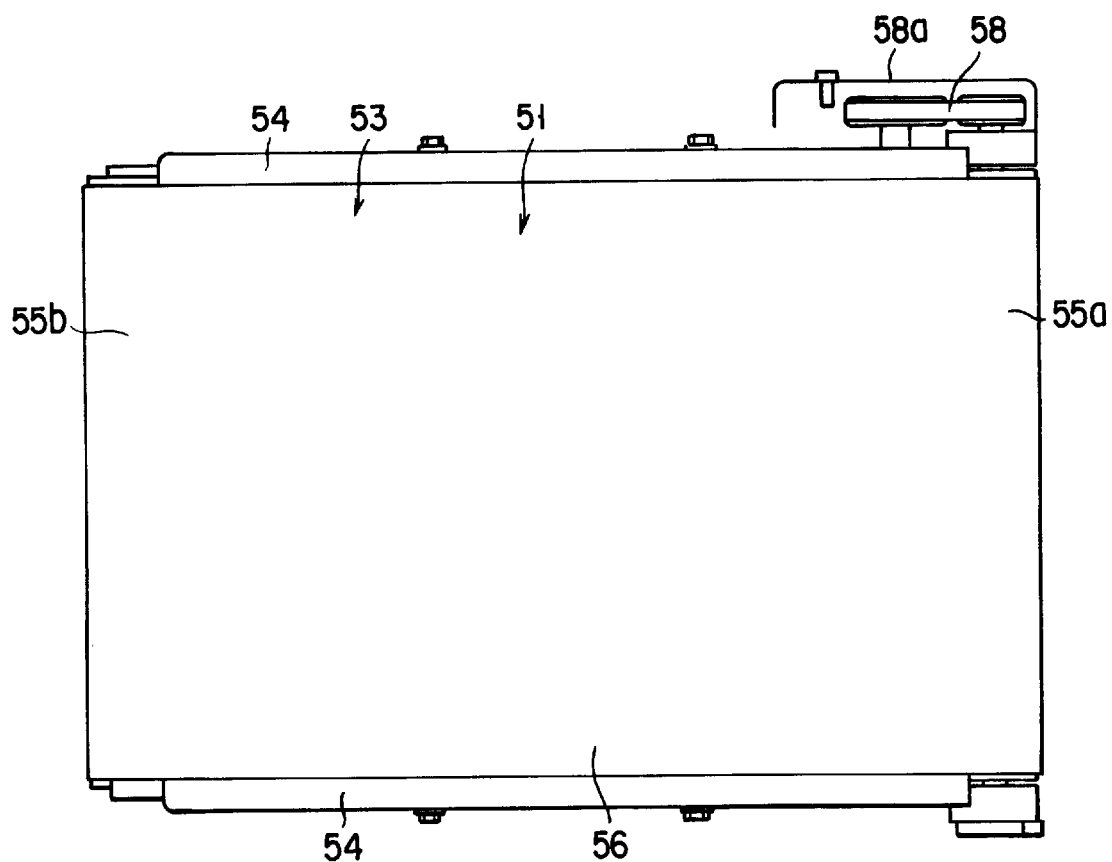
FIGS. 16A and 16B are plane and side views showing a conventional conveyor.
Figure 16B:
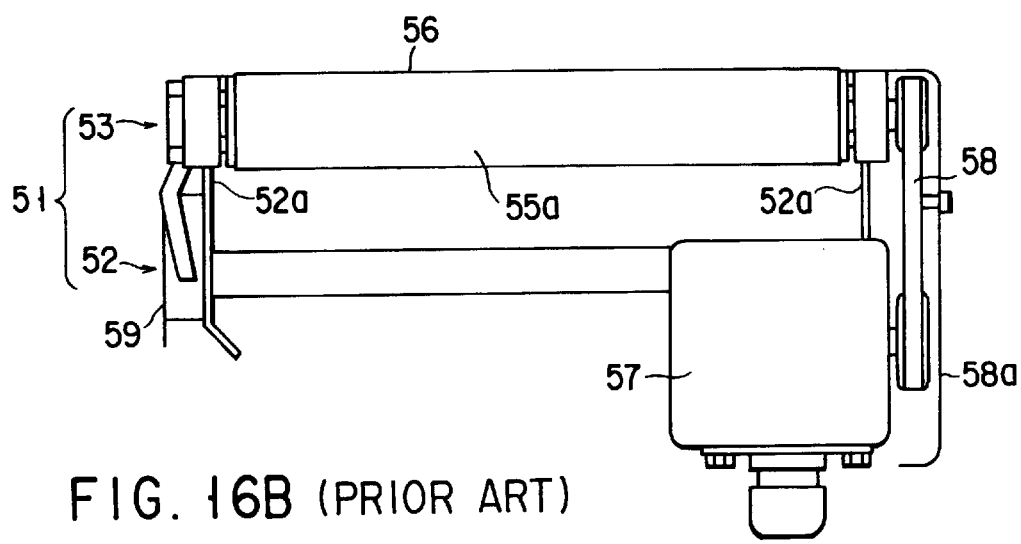

FIG. 15 is a schematic front view for explaining the change of the device length of the X-ray foreign-body detector according to the third embodiment of the present invention.

As shown in FIG. 15, a metal box 306 of the conveyor part 303 and an X-ray detection part 302 contained therein may be kept fixed to the casing 305.

Further, with respect to this metal box 306, a front roller support part 311 and a rear roller support part 312 are replaced with new ones which comply with a desired conveying distance.

Specifically, the new front roller support part 311 and rear roller support part 312 are replaced with those ones that respectively have desired lengths in the conveying direction.

In addition, a front cover 332, rear cover 333, and main cover (not shown) attached to the casing 305 are replaced with those ones that respectively correspond to the new device length.

As shown in the figure, those front and rear covers 332 and 333 that respectively project by predetermined amounts in the conveying direction in correspondence with the device length are used.

Although not shown in the figure, the cover used as the main cover has such a shape that covers the main surface sides of the front cover 332 and rear cover 333.

These front cover 332 and rear cover 333 are fixed to the casing 305 with screws and can easily be replaced.

At the time of replacement, slave rollers 308a, 308b, and 308c and a drive roller unit 308U, which are attached to the front and rear roller support parts 311 and 312, need not be replaced newly but may be directly attached to the replaced new front roller support part 311 and rear roller support part 312.

At first, the main cover is opened. The fixing mechanism 318 is released, and the side plate 313 is slid. The tension of the conveyor belt is reduced, and the conveyor belt 310 is detached. Thereafter, the slave rollers 308a, 308b, and 308c are detached from the notch parts (not shown) of the support members (not shown).

The drive roller unit 308U can detached by merely releasing the fixing mechanism (not shown). At this time, the connection with the motor unit (not shown) can be simultaneously released by means of the couplings (not shown) of at the connection part (not shown), so the motor unit can be detached.

Thereafter, the front roller support part 311 and the rear roller support part 312 can each be lifted upward, and the engagement between the holes 315 and the engaging parts 316 (including bolts and washers) in the side of the metal box 306 is released.

Thereafter, the front cover 332, rear cover 333, and main cover are detached, and a new front cover 332, new rear cover 333, and new main cover that provide a new device length are attached to the casing 305.

Thereafter, a new front roller support part 311 and new rear roller support part 312 are attached to the metal box 306.

At this time, the fixing plates 311a and 312a are moved downward with their holes 315 engaged with the engaging parts 316 (including bolts and washers) of the metal box 306.

Next, the slave rollers 308a, 308b, and 308c are attached to the notch parts of the support members 311c, etc.

Also, the drive roller unit 308U is positioned and set on the support parts (not shown) of the support members 312c, etc. and the fixing mechanism is operated and fixed.

At this time, the drive roller 308d is simultaneously connected with the motor unit by the couplings at the connection part.

Further, a belt 310 matched with a new conveying distance is attached, and thereafter, the fixing mechanism 318 is fixed and operated to slide the side plate 313, so that a tension is applied to the conveying belt 310.

In the manner as described above, the device length can be changed. To make this change, the parts that should be replaced are only the support members 311 and 312, conveyor belt 310, front cover 332, rear cover 333, and main cover.

Therefore, the device length can be changed without detaching or attaching the main part of the metal box 306 in which the X-ray detection part is contained, i.e., the X-ray detection unit.

As a result, the position of the X-ray detection part 302 is not changed but its position relative to the X-ray generation part 301 is kept unchanged so that adjustment or the like of the radiating position is not necessitated.

Further, the device length can be changed with the setting position of the casing 305 fixed. The device length can be changed through the easy procedure described above and an object to be inspected can be transferred and received between devices in the front and rear stages, even in case where the arrangement interval between the front stage side and the rear stage side is changed.

In the third embodiment described above, explanation has been made to a structure in which the front roller support part 311 and the rear roller support part 312 which are detachable from and attachable to the metal box 306 are replaced when changing the device length. However, the device length can be changed in other manners than the structure limited to the structure described above.

For example, when the device length is elongated to be longer than it was before, the structure may be arranged so as to use directly the front roller support part 311 and the rear roller support part 312 without changes.

In this case, the structure is arranged such that a joint member is provided between the front surface 6b and rear surface 6c of the metal box 306 and the front roller support part 311 and rear roller support part 312 and the front roller support part 311 and rear roller support part 312 are fixed to the metal box 306 through the joint member.

As the joint member, a plurality of holes 315 described above as well as engaging parts 316 are provided.

According to the X-ray foreign-body detector according to the third embodiment of the present invention, only the roller support parts and the conveyor belt need to be replaced with those ones that comply with a desired device length in order to change the device length. The device length can thus simply and easily changed only by replacement of a minimum number of parts.

Since the roller support parts are structured to be detachable from and attachable to the metal box which seals and contains the x-ray detection part. When the device length is changed, it is unnecessary to change the X-ray detection part and the device length can be changed while preventing leakage of X-rays from the X-ray detection part to the outside.

In this manner, the device length can be changed without replacing the entire apparatus.

Also, it is possible to obtain a device length necessary for a new device, in case of replacing an old device set between the devices in the front and rear stages.

Also, according to the X-ray foreign-body detector according to the third embodiment of the present invention, it is only necessary to attach a replacement cover corresponding to a conveying distance, to the casing, so that the conveyor part can be shielded easily from the X-rays.

In addition, in the X-ray foreign-body detector according to the third embodiment of the present invention, engaging parts are provided for the metal box and the roller support parts, so that the roller support parts can be easily detached and attached.

Also, in the X-ray foreign-body detector according to the third embodiment of the present invention, the drive roller is constructed in form of a unit and can therefore be simply detached from and attached to a roller support part, so that changing the device length can be achieved more easily.

Also, in the X-ray foreign-body detector according to the third embodiment of the present invention, a connection part is provided at an end part of the drive roller so that the drive force of the motor can be transmitted freely. The drive roller unit can be detached and attached more easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray foreign-body detector comprising:
   a casing:
      an X-ray generation part provided inside the casing; and an X-ray detection unit integrally including an X-ray detection part, which detects X-rays and a conveyor part, which conveys an object to be inspected, for detecting a foreign body contained in the object by receiving the X-rays, which are radiated from the X-ray generation part to the object conveyed by the conveyor part and is transmitted through the object, by means of the X-ray detection part, the X-ray detection part and the conveyor part being integrally attached to a predetermined part of the casing, such that the X-ray detection part and the conveyor part are freely attachable and detachable, wherein the X-ray detection unit comprises
an X-ray detection part container made of metal, which has at least an upper surface, a lower surface opposed to the upper surface, and front and rear surfaces which connect the upper and lower surfaces in both sides in a longitudinal direction, and in which a slit extending in a lateral direction to allow the X-rays to penetrate through the upper surface is formed in the upper surface, and the X-ray detection part is provided inside, a front roller support part extending forward in the longitudinal direction of the X-ray detection part container and attached to the X-ray detection part container, a rear roller support part extending rearward in the longitudinal direction of the X-ray detection part container and attached to the X-ray detection part container, a front roller detachably and attachably included in the front roller support part, a rear roller detachably and attachably included in the rear roller support part, and a conveyor belt tensioned around the front and rear rollers, surrounding the X-ray detection part container, and supported on the upper surface of the X-ray detection part container in a state in which the object is mounted thereon, one of the front and rear rollers being constructed as a drive roller and the other one being constructed as a slave roller.

2. The detector according to claim 1, wherein the X-ray detection unit further comprises a drive roller unit provided in parallel with the drive roller, the drive roller unit comprising,
a drive roller,
a pair of bearing parts provided at both ends of the drive roller, and
a fixing shaft to which the pair of bearing parts are fixed, the drive roller unit being detachably attached to the x-ray detection part container.

3. The detector according to claim 2, wherein the X-ray detection part container is provided with engaging grooves in which with one of the bearing parts and the fixing shafts are engaged and positioned to fix the drive roller unit.

4. The detector according to claim 2, wherein the X-ray detection part container is provided with a fixing mechanism which is engaged with the fixing shaft thereby to fix and hold the drive roller unit in relation to the casing.

5. The detector according to claim 2, wherein the X-ray detection unit further comprises a connection part provided at an end part of a rotation shaft of the drive roller, to transmit the drive force of the motor and to enable separation, such that the drive roller unit can be freely detached and attached by separation at the connection part.

6. The detector according to claim 5, wherein the connection part is constructed by a pair of couplings fixed respectively to an output shaft of the motor and the rotation shaft of the drive roller, and the drive force is transmitted by junction of the couplings with each other.

7. The detector according to claim 6, wherein the X-ray detection unit further comprises a protection case and a receiving seat provided for the drive roller and the motor, such that the protection case and the receiving seat are respectively coaxial with the pair of couplings, enable positioning of axial centers of the pair of couplings, and cover the pair of couplings.

8. The detector according to claim 2, wherein the X-ray detection part is sealed and contained in the X-ray detection part container.

9. The detector according to claim 8, wherein
one slave roller among the one drive roller and three slave rollers is arranged at a side part of the X-ray detection part container; and the other two slave rollers of the three slave rollers are arranged at another side part of the x-ray detection part container.

10. The detector according to claim 9, wherein
engaging grooves in which the two slave rollers arranged at another side part are engaged, are formed in the X-ray detection part container, and a slide plate which can be freely slid is provided in a side of the side part.

11. The detector according to claim 1, wherein the roller support parts corresponding to a conveying distance are respectively installed at positions in front and rear of the X-ray detection part container, and a conveyor belt having a corresponding conveying distance is installed together, thereby to make the conveying distance freely changeable.

12. The detector according to claim 11, wherein the X-ray detection part container is provided with a cover which has a length corresponding to the conveying distance of the conveyor part and prevents leakage of X-rays.

13. The detector according to claim 11, wherein an engaging part for engaging and releasing each other of the X-ray detection part container and the front and rear roller support parts is provided on a joint surface between the X-ray detection part container and the front and rear roller support parts.

14. The detector according to claim 11, wherein a drive roller unit for conveying and driving the conveyor belt is provided detachably and attachably at the front and rear roller support parts, and the drive roller unit comprises a pair of bearing parts provided at both ends of the drive roller; and a fixing shaft, for making the pair of bearing parts respectively fixed to the fixing shaft.

15. The detector according to claim 14, wherein a connection part which transmits the drive force of a motor and can be freely separated is provided at an end part of a rotation shaft of the drive roller.

* * * * *